(12) United States Patent
Pandey et al.

(10) Patent No.: US 9,045,488 B2
(45) Date of Patent: Jun. 2, 2015

(54) PAA NANOPARTICLES FOR TUMOR TREATMENT AND IMAGING

(75) Inventors: Ravindra K. Pandey, East Amherst, NY (US); Anurag Gupta, Hamburg, NY (US); Penny Joshi, Amherst, NY (US); Manivannan Ethirajan, Buffalo, NY (US); Avinash Srivatsan, Buffalo, NY (US)

(73) Assignee: Photolitec, LLC, East Amherst, NY (US)

( * ) Notice: Subject to any disclaimer, the term of this patent is extended or adjusted under 35 U.S.C. 154(b) by 331 days.

(21) Appl. No.: 13/544,558

(22) Filed: Jul. 9, 2012

(65) Prior Publication Data

US 2014/0011989 A1    Jan. 9, 2014

(51) Int. Cl.
*C07D 487/22* (2006.01)
*C07D 471/22* (2006.01)
*C07H 13/08* (2006.01)

(52) U.S. Cl.
CPC ............ *C07D 487/22* (2013.01); *C07D 471/22* (2013.01); *C07H 13/08* (2013.01)

(58) Field of Classification Search
CPC ..... C07D 487/22; C07D 471/22; C07H 13/08
See application file for complete search history.

(56) References Cited

U.S. PATENT DOCUMENTS

| 8,562,944 B2 * | 10/2013 | Pandey et al. ................ 424/1.11 |
| 2011/0091373 A1 * | 4/2011 | Pandey et al. ................ 424/1.11 |
| 2011/0206613 A1 * | 8/2011 | Wiehe et al. ................... 424/9.1 |

* cited by examiner

*Primary Examiner* — Elli Peselev
(74) *Attorney, Agent, or Firm* — Michael L. Dunn

(57) ABSTRACT

A tetrapyrrolic photosensitizer and imaging compound having a substituent other than hydrogen at its 10 carbon atom which substituent may contain a PAA nanoparticle.

14 Claims, 17 Drawing Sheets

PAA NANOPARTICLES FOR TUMOR TREATMENT AND IMAGING

BACKGROUND OF THE INVENTION

Nanoscience is being developed in conjunction with advanced medical science for further precision in diagnosis and treatment. Multidisciplinary biomedical scientific teams including biologists, physicians, mathematicians, engineers and clinicians are working to gather information about the physical properties of intracellular structures upon which biology's molecular machines are built. A new emphasis is being given to moving medical science from laboratory to the bedside and the community. This platform development program brings together an outstanding laboratory that is pioneering biomedical applications of PAA (polyacrylic acid) nanovectors (Kopelman), together with an innovative porphyrin chemistry and a world-class PDT (photodynamic therapy) group at RPCI that is highly experienced in the high volume screening and in vitro/in vivo evaluation of novel compounds, and in developing new therapies from the test tube to FDA approval for clinical use. Although nanoplatforms and nanovectors (i.e. a nanoplatform that delivers a therapeutic or imaging agent) for biomedical applications are still evolving, they show enormous promise for cancer diagnosis and therapy. The approach has been the subject of several recent reviews. Therapeutic examples include nanoparticles (NPs) containing PDT agents, folate receptor-targeted, boron containing dendrimers for neutron capture and NP-directed thermal therapy. Recently, therapeutic and imaging potential of encapsulated, post-loaded and covalently linked photosensitizer-NPs have been evaluated. In PAA NP the post-loading efficiency showed enhanced in vitro/in vivo therapeutic and imaging potential. PAA NP have core matrixes that can readily incorporate molecular or small NP payloads, and can be prepared in 10-150 nm sizes, with good control of size distributions. The surfaces of NPs can be readily functionalized, to permit attachment of targeting ligands, and both are stable to singlet oxygen (1O2) produced during PDT. PAA-NP have the advantages of (1) A relatively large knowledge base on cancer imaging, PDT, chemical sensing, stability and biodegradation. (2) No known in-vivo toxicity. (3) Long plasma circulation time without surface modification, but with biodegradation and bioelimination rates controllable via the type and amount of selective cross-linking (introduced during polymerization inside reverse micelles). (4) Scale-up to 400 g material has been demonstrated, as well as storage stability over extended periods. Limitations include relative difficulty in incorporating hydrophobic compounds (although we have accomplished this), leaching of small hydrophilic components unless they are "anchored", and unknown limitation on bulk tumor permeability because of hydrogel swelling.

The major challenge of cancer therapy is preferential destruction of malignant cells with sparing of the normal tissue. Critical for successful eradication of malignant disease are early detection and selective ablation of the malignancy. PDT is a clinically effective and still evolving locally selective therapy for cancers. The utility of PDT has been demonstrated with various photosensitizers for multiple types of disease. It is FDA approved for early and late stage lung cancer, obstructive esophageal cancer, high-grade dysplasia associated with Barrett's esophagus, age-related macular degeneration and actinic keratoses. PDT employs tumor localizing PSs that produce reactive $1O_2$ (singet oxygen) upon absorption of light which is responsible for the destruction of the tumor. Subsequent oxidation-reduction reactions also can produce superoxide anions, hydrogen peroxide and hydroxyl radicals which contribute to tumor ablation. Photosensitizers have been designed which localize relatively specifically to certain subcellular structures such as mitochondria, which are highly sensitive targets. On the tumor tissue level, direct photodynamic tumor cell kill, destruction of the tumor supporting vasculature and possibly activation of the innate and adaptive anti-tumor immune system interact to destroy the malignant tissue. The preferential killing of the targeted cells (e.g. tumor), rather than adjacent normal tissues, is essential for PDT, and the preferential target damage achieved in clinical applications is a major driving force behind the use of the modality. The success of PDT relies on development of tumor-avid molecules that are preferentially retained in malignant cells but cleared from normal tissues. Clinical PDT initially was developed at Roswell Park Cancer Institute (RPCI), and we have one of the world's largest basic and clinical research programs. The RPCI group developed Photofrin®, the first generation FDA approved hematoporphyrin-based compound. Subsequently, our group has investigated structure activity relationships for tumor selectivity and photosensitizing efficacy, and used the information to design new PSs (photosensitizers) with high selectivity and desirable pharmacokinetics. Although the mechanism of porphyrin retention by tumors in not well understood, the balance between lipophilicity and hydrophilicity is recognized as an important factor. In our efforts to develop effective photosensitizers with the required photophysical characteristics, we used chlorophyll-a and bacteriochlorophyll-a as the substrates. Extensive QSAR studies on a series of the alkyl ether derivatives of pyropheophorbide-a (660 nm) led to selection of the best candidate, HPPH (hexyl ether derivative) 8,9, now in promising Phase II clinical trials. Our PS development now extends to purpurinimide (700 nm) and bacteriopurpurinimde (780-800 nm) series with high 1O2 producing capability 10-13 Long wavelength absorption is important for treating large deep-seated tumors, because longer wavelength light increases penetration and minimizes the number of optical fibers needed for light delivery within the tumor Tetrapyrrolic photosensitizers used in accordance with the present invention are based upon the tetrapyrrolic structure shown below:

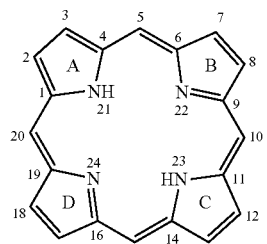

IUPAC NOMENCLATURE

The penetration of light through tissue increases as its wavelength increases between 630 and 800 nm. Once light has penetrated tissue more than 2-3 mm it becomes fully diffuse (i.e. non-directional). In diffusion theory, the probability that a photon will penetrate a given distance into tissue is governed by the probability per unit path. The intrinsic absorption of most tissues is dominated by hemoglobin and deoxyhemoglobin, with the strong peaks of the absorption bands at wavelengths shorter than 630 nm. The tails of these bands extend beyond 630 nm and grow weaker with increasing wavelength. Thus the probability of a photon being absorbed by endogenous chromophores decreases with increasing wavelength from 630-800 nm and the scattering also decreases with wavelength 14 resulting in the very large increase in light penetration at ~600 to 800 nm.

Tetrapyrrolic photosensitizers have several very desirable properties as therapeutic agents deliverable by NP: (1) Often only a very small fraction of administered targeted drug makes it to tumor sites and the remainder can cause systemic toxicity. However, tetrapyrrolic PDT provides dual selectivity in that the PS is inactive in the absence of light and is innocuous without photoactivation. Thus the PS contained by the NP can be locally activated at the site of disease. (2) PDT effects are due to production of 1O2, which can readily diffuse from the pores of the NP. Thus, in contrast to usual chemotherapeutic agents, release of encapsulated drug from the NP, is not necessary. Instead, stable NP with long plasma residence times can be used, which increases the amount of drug delivered to the tumors. (3) PDT is effective regardless of the intracellular location of the PS. While mitochondria are a principal target of 1O2, PS incorporated in lysosomes are also active the photodynamic process causes rupture of the lysosomes with release of proteolytic enzymes and redistribution of the PS within the cytoplasm. NP platforms also provide significant advantages for PDT: (1) High levels of imaging agents can be combined with the PS in the NP permitting a "see and treat" approach, with fluorescence image guided placement of optical fibers to direct the photoactivating light to large or subsurface tumors, or to early non clinically evident disease. (2) It is also possible to add targeting moieties, such as cRGD or F3 peptide to the NP so as to increase the selective delivery of the PS. (3) The NP can carry large numbers of PS, and their surface can be modified to provide the desired hydrophilicity for optimal plasma pharmacokinetics. Thus, they can deliver high levels of PS to tumors, reducing the amount of light necessary for tumor cure.

Unfortunately it has been found that conjugating a tetrapyrrolic photosensitizer with PAA nanoparticles by usual attachment sites, i.e. through the A-D rings, results in inhibition of photodynamic effect. Further up to now, it has not been possible to attach any groups or conjugate through the carbon links between the A-D rings of the tetrapyrrolic structure, i.e. through the 5, 10, 15 or 20 carbon atoms and it was not known or surmised whether or not such a link, even if possible, would have a negative, positive or no effect.

Multiple, complementary techniques for tumor detection, including magnetic resonance, scintigraphic and optical imaging are under active development. Each approach has particular strengths and advantages. Optical imaging includes measurement of absorption of endogenous molecules (e.g. hemoglobin) or administered dyes, detection of bioluminescence in preclinical models, and detection of fluorescence from endogenous fluorophores or from targeted exogenous molecules. Fluorescence, the emission of absorbed light at a longer wavelength, can be highly sensitive: a typical cyanine dye with a lifetime of 0.6 nsec can emit up to 1032 photons/second/mole. A sensitive optical detector can image <103 photons/second. Thus even with low excitation power, low levels of fluorescent molecular beacons can be detected. A challenge is to deliver the dyes selectively and in high enough concentration to detect small tumors. Use of ICG (isocyanine green dye) alone to image hypervascular or "leaky" angiogenic vessels around tumors has been disappointing, due to its limited intrinsic tumor selectivity. Multiple approaches have been employed to improve optical probelocalization, including administering it in a quenched form that is activated within tumors, or coupling it to antibodies or small molecules such as receptor ligands. Recent studies have focused on developing dye conjugates of small bioactive molecules, to improve rapid diffusion to target tissue and use combinatorial and high throughput strategies to identify, optimize, and enhance in vivo stability of the new probes. Some peptide analogs of ICG derivatives have moderate tumor specificity and are entering pre-clinical studies. However, none of these compounds are designed for both tumor detection and therapy. It is important to develop targeting strategies that cope with the heterogeneity of tumors in vivo, where there are inconsistent and varying expressions of targetable sites.

Photosensitizers (PS) generally fluoresce and their fluorescence properties in vivo has been exploited for the detection of early-stage cancers in the lung, bladder and other sites 17 For treatment of early disease or for deep seated tumors the fluorescence can be used to guide the activating light. However, PS are not optimal fluorophores for tumor detection for several reasons: (i) They have low fluorescence quantum yields (especially the long wavelength photosensitizers related to bacteriochlorins). Efficient PS tend to have lower fluorescence efficiency (quantum yield) than compounds designed to be fluorophores, such as cyanine dyes because the excited singlet state energy emitted as fluorescence is instead transferred to the triplet state and then to molecular oxygen. (ii) They have small Stokes shifts. Porphyrin-based PS have a relatively small difference between the long wavelength absorption band and the fluorescence wavelength (Stokes shift), which makes it technically difficult to separate the fluorescence from the excitation wavelength. (iii) Most PS have relatively short fluorescent wavelengths, <800 nm, which are not optimal for detection deep in tissues.

In a separate study certain bifunctional conjugates have been developed that use tumor-avid tetrapyrrolic PS to target NIR (near infrared) fluorophores to tumor. The function of the fluorophore is to visualize the tumor location and treatment site. The presence of the PS allows subsequent tumor ablation. The optical imaging allows the clinician performing PDT to continuously acquire and display patient data in real-time. This "see and treat" approach may determine where to treat superficial carcinomas and how to reach deep-seated tumors in sites such as the breast, lung and brain with optical fibers delivering the photo-activating light. Due to a significant difference between imaging and therapeutic doses, the use of a single molecule that includes both modalities is problematic. However, with PAA NPs we were able to solve this problem but, as previously discussed, conjugation to the nanoparticle decreases PDT efficiency.

A photosensitizer (PS) with increased selectivity and longer wavelength could be a more suitable candidate for brain and deeply seated tumors (especially breast, brain and lung). The evolution of light sources and delivery systems is also critical to the progression of photodynamic therapy (PDT) in the medical field. Two different techniques: interstitial and intracavitary light delivery have been used for treatment of brain tumors. Powers et al 26 using interstitial PDT on patients with recurrent brain tumors showed that the majority of patients had tumor recurrence within two months of treatment. However, it was later observed that treatment failures appeared to occur outside the region of the effective light treatment. Chang et al reported an effective radius of tumor cell kill in 22 glioma patients of 8 mm compared with the 1.5 cm depth of necrosis noted by Pierria with the intracavitary illumination method. It is believed that tumor resection is important so that the numbers of tumor cells remaining to treat are minimized. With stereotactic implantation of fibers for interstitial PDT there is no cavity to accommodate swelling and a considerable volume of necrotic tumor which causes cerebral edema. However, cerebral edema can be readily controlled with steroid therapy. Compared to chemotherapy and radiotherapy, patients with brain tumors treated with PDT have definitely shown long-term survival, whereas glioma patients treated with adjuvant chemotherapy or radiotherapy do not show additional benefits as reported by Kostron et al. and Kaye et al. On the basis of our preliminary data, the αvβ3 targeted NPs may improve tumor-selectivity and PDT outcome.

The prognosis for patients with malignant brain tumors is linked to the completeness of tumor removal. However, the borders of tumors are often indistinguishable from surrounding brain tissue so tumor excision is highly dependent upon the neurosurgeon's judgment. To identify tumors, neurosurgeons use diagnostic imaging methods such as Computed Tomography (CT) or Magnetic Resonance Imaging (MRI), which enhance the contrast between tumor and surrounding brain tissue. However, there are frequently discrepancies between intraoperative observations of tumor margins and preoperative diagnostic imaging studies. Unlike CT and MRI, intraoperative ultrasound can provide real-time information to locate the tumor and define its volume. However, once resection commences is also limited by signal artifacts caused by blood and surgical trauma limit tumor identification at the resection margin. Intraoperative MRI allows the neurosurgeon to obtain images during surgery, which can improve the completeness of the tumor resection, however microscopic disease is still not detected. In an ideal situation, the surgeon would perform the brain tumor resection with continuous guidance from high-contrast fluorescence from the tumor observed directly in the resection cavity.

BRIEF SUMMARY OF THE INVENTION

The present invention relates to a novel tetrapyrrolic photosensitizer having a substituent attached through carbon atom 20 between the A and D rings of the basic tetrapyrrolic structure and further relates to polyacrylic acid (PAA) nanoparticles containing a photosensitizer conjugated with a PAA nanoparticle through carbon atom 20 between the A and D rings of the basic tetrapyrrolic structure and an imaging enhancing agent also containing a fluorescent imaging agent. The preferred fluorescent imaging agent is a cyanine dye.

The photosensitizer is preferably a tetrapyrrolic photosensitizer having the structural formula:

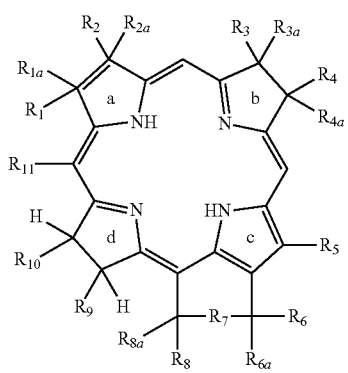

or a pharmaceutically acceptable derivative thereof, wherein:
$R_1$ is hydrogen or lower alkyl of 1 through 8 carbon atoms;

$R_2$ is hydrogen, lower alkyl of 1 through 8 carbon atoms, —C(O)$R_a$ or —COOR$_a$ or —CH(CH$_3$)(OR$_a$) or —CH(CH$_3$)(O(CH$_2$)$_n$XR$_a$) where $R_a$ is hydrogen, lower alkyl of 1 through 8 carbon atoms, alkenyl of 1 through 8 carbon atoms, cycloalkyl; —CH=CH$_2$, —CH(OR$_{20}$)CH$_3$, —C(O)Me, —C(=NR$_{20}$)CH$_3$ or —CH(NHR$_{20}$)CH$_3$ where X is an aryl or heteroaryl group;
n is an integer of 0 to 6;
where $R_{20}$ is lower alkyl of 1 through 8 carbon atoms, or 3,5-bis(trifluoromethyl)-benzyl; and $R_{1a}$ and $R_{2a}$ are each independently hydrogen or lower alkyl of 1 through 8 carbon atoms, or together form a covalent bond;

$R_3$ and $R_4$ are each independently hydrogen or lower alkyl of 1 through 8 carbon atoms;

$R_{3a}$ and $R_{4a}$ are each independently hydrogen or lower alkyl of 1 through 8 carbon atoms, or together form a covalent bond;

$R_5$ is hydrogen;

$R_6$ and $R_{6a}$ are each independently hydrogen or lower alkyl of 1 through 8 carbon atoms, or together form =O;

$R_7$ is a covalent bond, alkylene of 1 through 3 carbon atoms, azaalkyl, or azaaralkyl or =NR$_{21}$ where $R_{21}$ is 3,5-bis(tri-fluoromethyl)benzyl or —CH$_2$Y—R$^1$ or —YR$^1$ where Y is an aryl or heteroaryl group;

$R_8$ and $R_{8a}$ are each independently hydrogen or lower alkyl of 1 through 8 carbon atoms or together form =O;

$R_9$ and $R_{10}$ are each independently hydrogen, or lower alkyl of 1 through 8 carbon atoms and $R_9$ may be —CH$_2$CH$_2$COOR$^2$ where $R^2$ is an alkyl group that may optionally substituted with one or more fluorine atoms;

$R_{11}$ is phenyl;

each of $R_1$-$R_{11}$, may be substituted with one or more substituents each independently selected from Q, where Q is alkyl, haloalkyl, halo, or —COOR$_b$ where $R_b$ is hydrogen, alkyl, alkenyl, alkynyl, cycloalkyl, aryl, heteroaryl, araalkyl, or OR$_c$ where $R_c$ is hydrogen, alkyl, alkenyl, alkynyl, cycloalkyl, or aryl or CONR$_d$R$_e$ where $R_d$ and $R_e$ are each independently hydrogen, alkyl, alkenyl, alkynyl, cycloalkyl, or aryl, or NR$_f$R$_g$ where $R_f$ and $R_g$ are each independently hydrogen, alkyl, alkenyl, alkynyl, cycloalkyl, or aryl, or =NR$_h$ where $R_h$ is hydrogen, alkyl, alkenyl, alkynyl, cycloalkyl, or aryl, or is an amino acid residue;

each Q is independently unsubstituted or is substituted with one or more substituents each independently selected from $Q_1$, where $Q_1$ is alkyl, haloalkyl, halo, pseudohalo, or —COOR$_b$ where $R_b$ is hydrogen, alkyl, alkenyl, alkynyl, cycloalkyl, aryl, heteroaryl, araalkyl, or OR$_c$ where $R_c$ is hydrogen, alkyl, alkenyl, alkynyl, cycloalkyl, or aryl or CONR$_d$R$_e$ where $R_d$ and $R_e$ are each independently hydrogen, alkyl, alkenyl, alkynyl, cycloalkyl, or aryl, or NR$_f$R$_g$ where $R_f$ and $R_g$ are each independently hydrogen, alkyl, alkenyl, alkynyl, cycloalkyl, or aryl, or =NR$_h$ where $R_h$ is hydrogen, alkyl, alkenyl, alkynyl, cycloalkyl, or aryl, or is an amino acid residue.

The photosensitizer may be conjugated with an image enhancing agent prior to incorporation into the nanoparticle, after incorporation into the nanoparticle or the photosensitizer and/or image enhancing agent may chemically bound to the nanoparticle and/or one or more of the photosensitizer and image enhancing agent may be physically bound to the nanoparticle.

Imaging enhancing agents may be for essentially any imaging process, e.g. examples of such imaging enhancing agents are discussed in the background of the invention previously discussed and in the list of references incorporated by reference herein as background art.

It is to be understood that other agents may be incorporated into the nanoparticle such as tumor targeting moieties and tumor inhibiting or tumor toxic moieties.

BRIEF DESCRIPTION OF THE SEVERAL VIEWS OF THE DRAWINGS

The patent or patent application file contains at least one drawing executed in color. Copies of this patent or patent application with color drawings will be provided by the Office upon request and payment of the necessary fee.

DETAILED DESCRIPTION OF THE INVENTION

Figure 1:
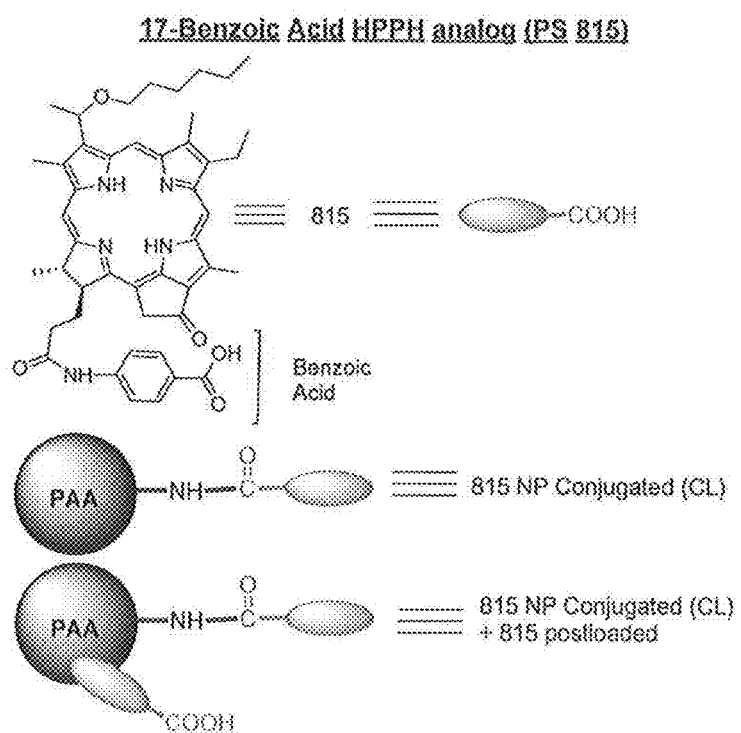
FIG. 1 shows a structural formula for 17-benzoic acid HPPH analog (PS815) having a substituent at the "17" carbon atom on the D ring suitable for conjugation with a PAA nanoparticle and showing such a conjugation through an amide link.
Figure 2:
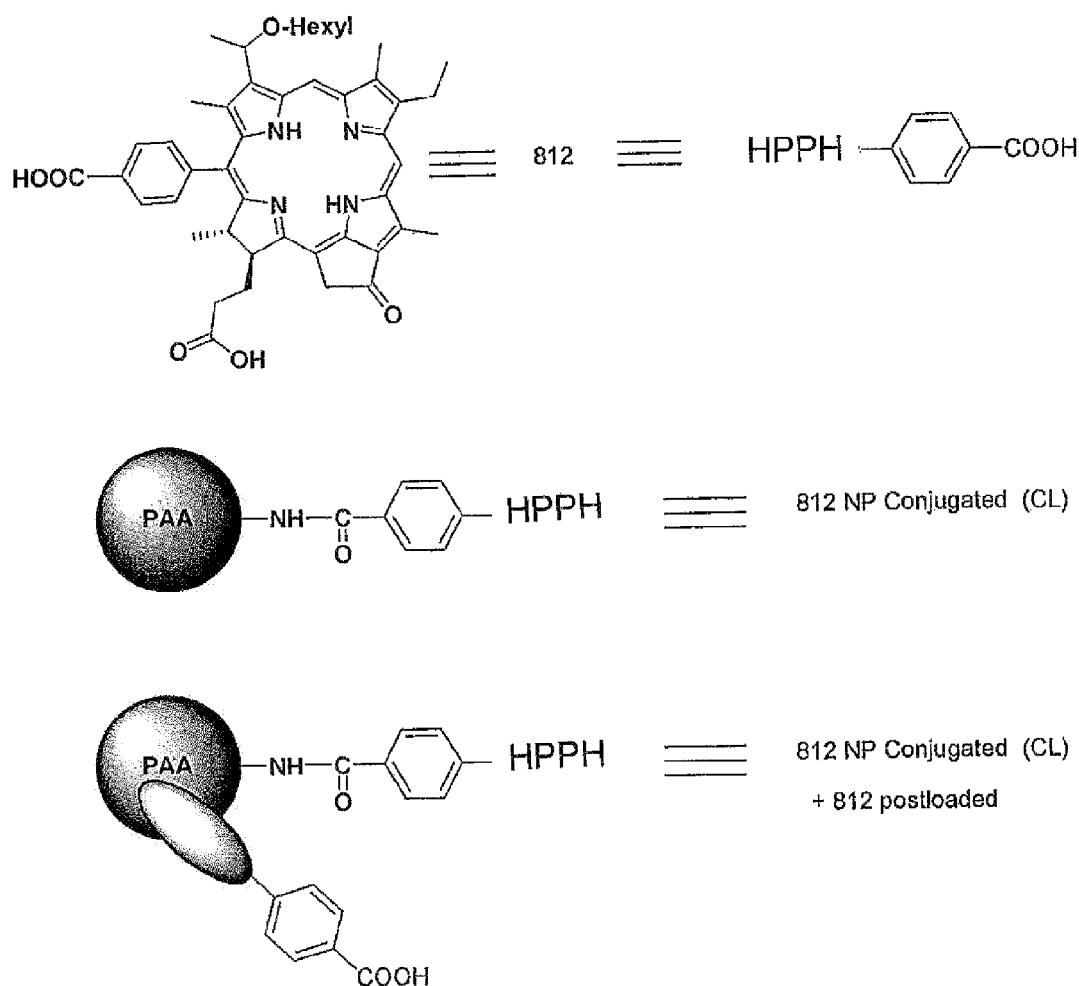
FIG. 2 shows a structural formula for 20-benzoic acid HPPH methyl ester analog (PS812) having a substituent at the "20" carbon atom between the A and D rings on the base ring of the tetrapyrrolic structure for conjugation with a PAA nanoparticle and showing such a conjugation through an amide link.

Previous inventions illustrate the utility of PAA nanoparticles for enhanced uptake of the imaging and phototherapeutic agents in tumors. We have also shown that certain cyanine dyes with limited tumor-avidity but desired photophysical properties on conjugating at the periphery of the nanoparticles show excellent fluorescence imaging ability. This could be due to the EPR effect (enhanced permeability and retention) of the nanoparticles, where the leaky tumor vessels help in accumulating the 30-35 nm size of the nanoparticles to tumor. In this invention, we investigated various approaches of conjugating photosensitizers, e.g HPPH containing a carboxylic acid group (—COOH) at the periphery of PAA nanoparticles bearing amino-functionalities, but the desired conjugate was obtained in a very low yield with limited reproducibility. However, modification of the HPPH moiety by introducing phenyl carboxylic acid either at position-17 or at position 20 gave the desired photosensitizer-nanoparticles conjugate in excellent yield. The nanoplatform containing photosensitizers in both peripheral conjugation and postloading showed excellent PDT efficacy and fluorescence imaging ability.

Following are descriptions of preparations of compounds in accordance with the invention.

Synthesis of PS 815 is made by known procedures by reaction of the —(CH$_2$)COOH group on the D ring at carbon atom 17 with paraamino benzoic acid (4-amino benzoic acid) to form an amide link to benzoic acid.

20-bromo-2-[1-hexyloxyethyl]-2-devinyl pyropheophorbide-a methyl ester (2)

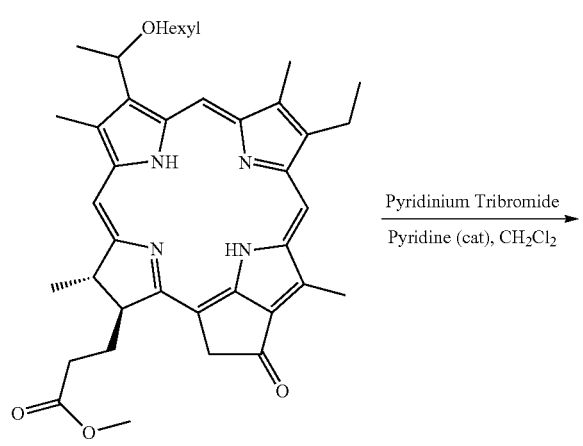

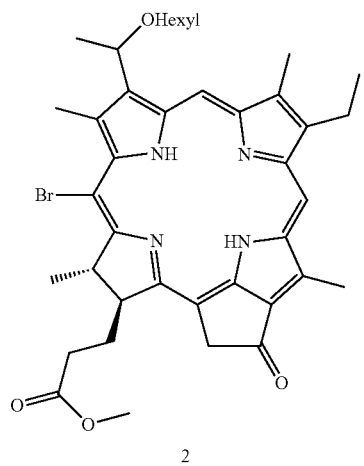

To a stirring solution of 1 (500 mg, 0.77 mmol, 1.0 eq) in 10 mL of dry dichloromethane was added pyridinium tribromide (271 mg, 0.85 mmol 1.1 eq). A few drops of pyridine were added to the mixture. The reaction mixture was stirred under an argon atmosphere and reaction progress was monitored via TLC. The organic layer was washed with sat. NaHCO$_3$/water/Brine (100 ml×1 each) and dried over Na$_2$SO$_4$, filtered and the solvent was removed under pressure. The resulting crude product was purified using silica gel chromatography by eluting with ethyl acetate and hexane to give 2. Yield 449 mg (80%). UV-vis max (in CH$_2$Cl$_2$): 675, 550, 414; $^1$H NMR (CDCl$_3$): δ 10.23 and 9.54 (s, 1H, meso-H), 6.00 (q, 1H CH(O-hexyl)-CH$_3$), 5.22 (s, 2H, CH-13$^1$), 4.93-4.87 (m, 1H, 18H); 4.27-4.24 (m, 1H, 17H), 3.73 (q, 2H, J=7.0 Hz, CH$_2$CH$_3$), 3.66 (s, 3H, 12-CH$_3$); 3.63 (s, 3H, 2-CH$_3$), 3.60 (s, 3H, —COCH$_3$), 3.32 (s, 3H, 7-CH$_3$), 2.63-2.18 (m, 4H, CH$_2$CH$_2$CO$_2$CH$_3$); 2.13 (split d, 3H, J=7.2 Hz, 3$^2$-CH$_3$), 1.72 (t, 3H, J=7.6 Hz, CH$_2$CH$_3$), 1.68 (m, 3H, 18$^1$-CH$_3$), 1.60 (t, 3H, —(CH$_2$)$_5$—CH$_3$), 1.4-0.8 (m, 10H, —(CH$_2$)$_5$), -1.78 and -1.82 (each brs, 2H NH); $^{13}$CNMR (100 MHz, CDCl$_3$): δ 195.98, 195.97, 173.43, 173.41, 171.6, 171.5, 160.9, 160.8, 153.4, 152.1, 147.97, 147.94, 144.5, 142.1, 141.9, 139.64, 139.62, 138.1, 138.0, 137.29, 137.28, 133.238, 133.230, 132.9, 132.7, 131.6, 129.52, 129.51, 106.71, 106.70, 106.6, 103.67, 103.63, 99.6, 94.6, 94.95, 77.45, 77.13, 76.8, 73.2, 93.1, 69.8, 69.7, 51.9, 51.75, 51.72, 51.6, 48.6, 31.82, 31.81, 31.80, 31.7, 30.92, 30.90, 30.3, 30.2, 29.8, 26.14, 26.13, 26.10, 25.0, 24.9, 22.658, 22.651, 22.64, 22.62, 20.88, 20.81, 19.4, 17.4, 17.1, 17.0, 14.06, 14.058, 14.050, 14.03, 14.01, 12.05, 12.04, 11.41, 11.40; EIMS (m/z): 730 (M+H). Elemental Anal. Calcd for C$_{40}$H$_{49}$BrN$_4$O$_4$: C, 65.84; H, 6.77; N, 7.68. Found: C, 65.98; H, 6.73; N, 7.52.

Synthesis of 20-tertbutoxycarbonyl phenyl-2-[1-hexyloxyethyl]-2-devinyl pyropheophorb-a methyl ester (3)

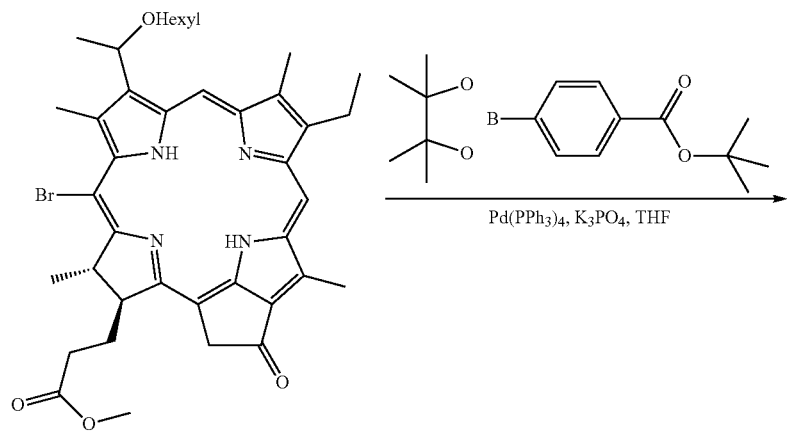

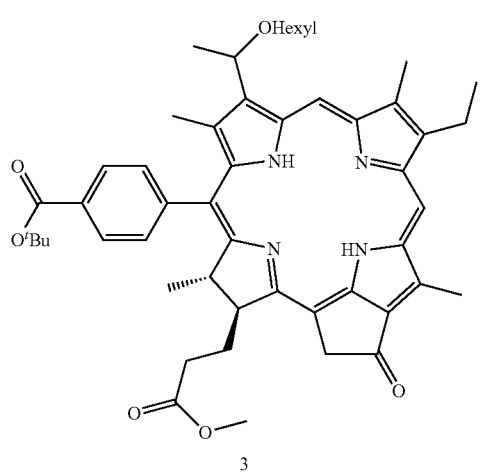

To a stirring solution of 2 (554 mg, 0.760 mmol, 1.0 eq) and potassium phosphate tribasic (3,207 mg, 15.20 mmol, 20 eq) in 30 mL of dry tetrahydrofuran (THF) was added boronic acid A (2,310 mg, 7.60 mmol, 10 eq) and palladium(0) tetrakistriphenyl phosphine (87.78 mg, 0.0760 mmol, 0.1 eq). The mixture was stirred under argon and brought to reflux for 16 hours. The reaction mixture was then brought back to room temperature and filtered to remove excess salt. The THF was then removed under vacuum. The resulting film was then reconstituted in 50 mL of dichloromethane. The solution was then washed with sat. NaHCO$_3$/water/brine (100 mL×1 each) and dried over sodium sulfate and the solvent was removed under pressure. The resulting crude product was purified using silica gel chromatography by eluting with ethyl acetate and hexane to give product 3. Yield=408.53 mg (65%).

UV-vis λ max (in CH$_2$Cl$_2$): 671, 613, 547, 515, 411; $^1$H NMR (CDCl$_3$): δ 10.16 & 10.12 (s, 1H, meso-H), 9.54 (s, 1H, meso-H); 8.41-8.43, 8.25-8.28, 8.20-8.23, 7.70-7.75, (Aromatic protons, 4H), 5.84 (q, 1H CH(O-hexyl)-CH$_3$), 5.22 (s, 2H, CH-13$^1$); 4.25-4.28 (m, 1H, 18H); 4.10-4.13 (m, 1H, 17H), 3.73 (q, 2H, J=7.0 Hz, CH$_2$CH$_3$); 3.65-3.76 (m and s, 5H, CH$_2$CH$_3$ & 2-CH$_3$), 3.60 (s, 6H, 12-CH$_3$ & —COCH$_3$), 3.31 (s, 3H, 7-CH$_3$); 2.53-2.57 (m, 2H), 2.37 (split d, 3H, 3$^2$-CH$_3$), 2.00 & 2.1 (dd, 3H), 1.72-1.68 (s & m, 12H, tertbutyl & CH$_2$CH$_3$); 1.61-1.67 (m, 3H, 18$^1$-CH$_3$); 1.60 (t, 3H, —(CH$_2$)$_5$—CH$_3$), 1.2-0.7 (multiplets, 10H, —(CH$_2$)$_5$); -1.51 and -1.57 (each brs, 2H NH);

20-carboxyphenyl-2-[1-hexyloxyethyl]-2-devinyl pyropheophorbide-a methyl ester (4) (PS812)

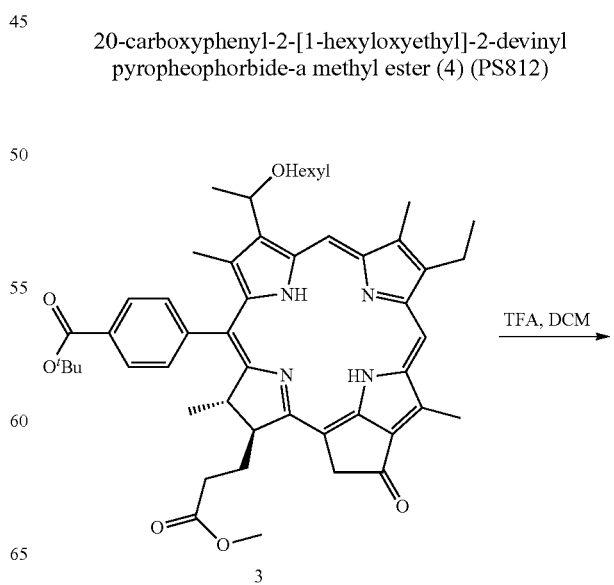

-continued

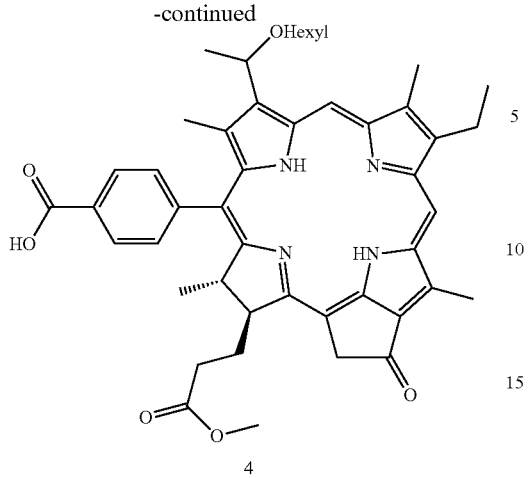

4

-continued

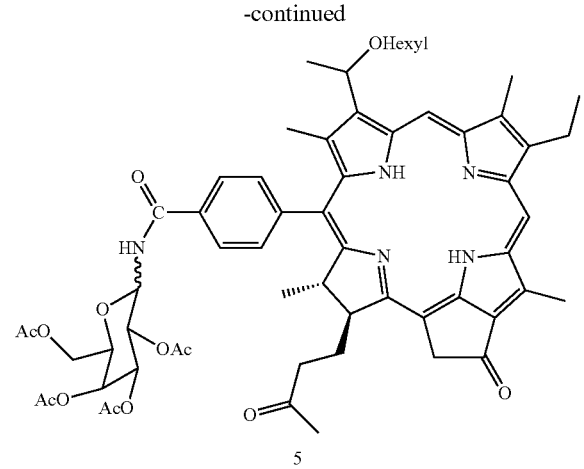

5

Compound 3 (50 mg, 0.08 mmol) was stirred in 70% trifluoroacetic acid:dichloromethane under argon for 2 hours. The trifluoroacetic acid was then removed under vacuum. The remaining film was reconstituted in dichloromethane (15 mL) and washed with NaHCO$_3$/water/brine (50 mL×1 each) and dried over sodium sulfate and the remaining solvent was removed under pressure. The resulting crude product was purified using preparative plate with dichloromethane and methanol (9:1) to give 4 in quantitative yield.

UV-vis λ max (in CH$_2$Cl$_2$): 671, 613, 547, 515, 411; $^1$H NMR (CDCl$_3$): δ 10.11 &10.15 (s, 1H, meso-H), 9.53 (s, 1H, meso-H); 8.30-8.61, 7.80 (phenyl ring protons, 4H), 5.80 (unresolved q, 1H CH(O-hexyl)-CH$_3$), 5.18 (s, 2H, CH-13$^1$), 4.26 & 4.07 (m, 2H, 18H & 17H), 3.73 (m, 2H, CH$_2$CH$_3$), 3.68 (s, 3H, 2-CH$_3$), 3.56 & 3.29 (s, 6H, 12-CH$_3$ & —COCH$_3$), 2.49-2.59 & 2.15-2.19 (bm, 4H, 17$^1$ CH$_2$ and 17$^2$ CH$_2$), 2.38 (s, 3H, 7-CH$_3$), 1.98, 2.12-2.19 (broad m, 6H, 3 CH$_3$ & 18$^1$-CH$_3$), 1.71-1.74 (distorted t, 3H, CH$_2$CH$_3$), 1.03-1.13, 0.84-0.93, 0.70, 0.77 (broad multiplets, 13H, —(CH$_2$)$_5$, −1.49 and −1.48 (each brs, 2H NH).

Compound 4 (50 mg, 0.066 mmole, 1.0 eq) was dissolved in DMF (10 ml). To it was added BOP (58.0 mg, 0.132 mmole, 2.0 eq) and amino galactose (46.0 mg, 0.132 mmole, 2.0 eq) and few drops of triethyl amine. Stirred for overnight at room temperature. The DMF was then removed under vacuum. The resulting film was then reconstituted in 50 mL of dichloromethane. The solution was then washed with sat. NaHCO$_3$/water/brine (100 mL×1 each) and dried over sodium sulfate and the solvent was removed under pressure. The resulting crude product was purified using preparative plate using methanol and DCM to give product 5.

20-bromo-2-[1-hexyloxyethyl]-2-devinyl pyropheophorbide-a (7)

Synthesis of 5

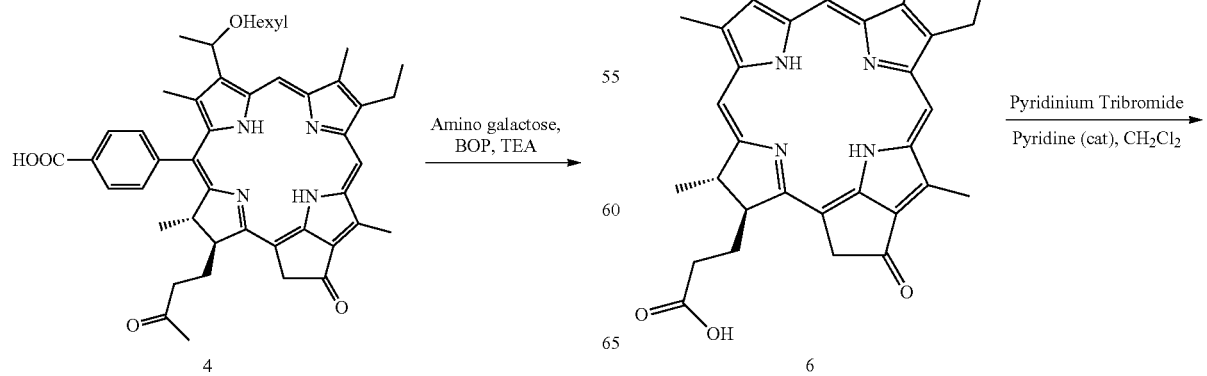

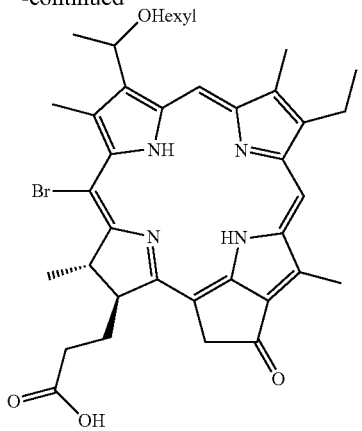

7

To a stirring solution of HPPH (500 mg, 0.78 mmol, 1.0 eq) in 30 mL of dry dichloromethane was added pyridinium tribromide (276 mg, 0.86 mmol 1.1 eq) and few drops of pyridine. The reaction mixture was stirred under an argon atmosphere and reaction progress was monitored via TLC. The organic layer was washed with sat. $NaHCO_3$/water/Brine (100 ml×1 each) and dried over $Na_2SO_4$, filtered and the solvent was removed under pressure. The resulting crude product was purified using silica gel chromatography hexane to give 7. Yield 325 mg (57%). UV-vis λ max (in $CH_2Cl_2$): 670, 551, 412; $^1$HNMR (400 MHz, $CDCl_3$): δ 10.11 (s, 1H, H-5), 9.54 (s, 1H, H-10), 5.93 (q, 1H, J=5.2 Hz, $CH_3C_H$Ohexyl), 5.23 (s, 2H, $C_H$-13$^1$), 4.89 (m, 1H, H-17), 4.26 (m, 1H, H-18), 3.67-3.72 (m, 2H, 8-$CH_2CH_3$), 3.65 (s, 3H, 7-$CH_3$), 3.61 (s, 3H, 2-$CH_3$), 3.58 (s, 3H, —$OCH_3$), 3.52 (s, 3H, COOMe), 3.30 (s, 3H, 12-$CH_3$), 2.63 (m, 1H, CH-17$^1$), 2.52 (m, 1H, H-17$^2$), 2.26 (m, 2H, H-17$^2$), 2.12 (split d, J=6.4 Hz, 3H, $CH_3$CHOMe), 1.70 (t, 3H, 8-$CH_2CH_3$, J=7.2 Hz), 1.60 (d, 3H, 18-$CH_3$, J=7.6 Hz), 0.84 (brs, 1H, NH), −1.78 (brs, 1H, NH); EIMS (m/z): 716 (M+H). Elemental Anal. Calcd for $C_{35}H_{39}BrN_4O_4$: C, 63.73; H, 5.96; N, 8.49. Found: C, 63.93; H, 5.69; N, 8.60.

Synthesis of 8

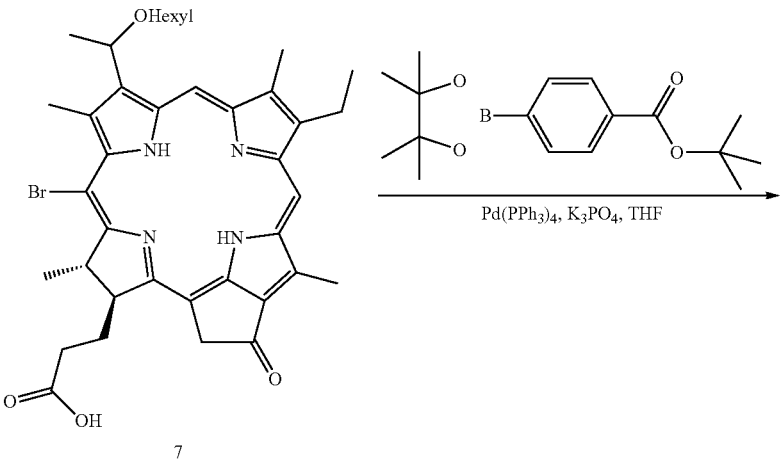

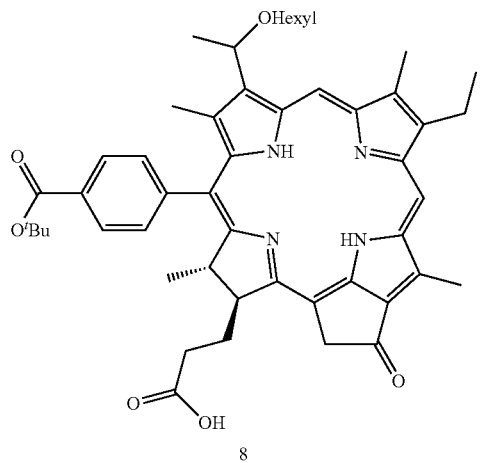

8

To a stirring solution of 7 (300 mg, 0.419 mmol, 1.0 eq) and potassium phosphate tribasic (1.7 g, 8.01 mmol, 15 eq) in 30 mL of dry tetrahydrofuran (THF) was added boronic acid (2.18 g, 7.19 mmol, 20 eq) and palladium(0) tetrakistriphenyl phosphine (103 mg, 0.089 mmol, 0.2 eq). The mixture was stirred under argon and brought to reflux for 16 hours. The reaction mixture was then brought back to room temperature and filtered to remove excess salt. The THF was then removed under vacuum. The resulting film was then reconstituted in 50 mL of dichloromethane. The solution was then washed with sat. NaHCO$_3$/water/brine (100 mL×1 each) and dried over sodium sulfate and the solvent was removed under pressure. The resulting crude product was purified using silica gel chromatography by eluting with methanol and DCM to give product 8. Yield=110 mg; UV-vis λ max (in CH$_2$Cl$_2$): 670, 614, 548, 515, 416; $^1$H NMR (CDCl$_3$): δ 10.12 & 10.08 (s, 1H, meso-H), 9.51 (s, 1H, meso-H); 8.37-8.39, 8.12-8.24, 8.17-8.21, 7.40-7.50, (Phenyl protons, 4H), 5.79-5.81 (q, 1H CH(O-hexyl)-CH$_3$), 5.20 (s, 2H, CH-13$^1$), 4.23-4.27 (m, 1H, 18H); 4.10-4.12 (m, 1H, 17H); 3.70-3.74 (m, 2H, CH$_2$CH$_3$), 3.67 (s, 3H, 2-CH$_3$), 3.28 (s, 3H, 7-CH$_3$); 2.56-2.60 (m, 2H, 17$^1$ CH$_2$), 2.47-2.45 (m, 2H, 17$^2$ CH$_2$), 2.34 (s, 3H, 12 CH$_3$), 2.22-2.28 (m, 2H, OCH$_2$CH$_2$), 1.98 & 2.10 (d, 3H, 3$^1$ CH$_3$), 1.72 (s, 9H, tertbutyl); 1.62-1.57 (m, 3H, 18$^1$-CH$_3$); 1.01-1.26 (multiplets, 10H, —(CH$_2$)$_5$, 0.70 & 0.79 (t, 3H, CH$_2$CH$_3$), −1.50 and −1.49 (each brs, 2H NH).

Synthesis of 9

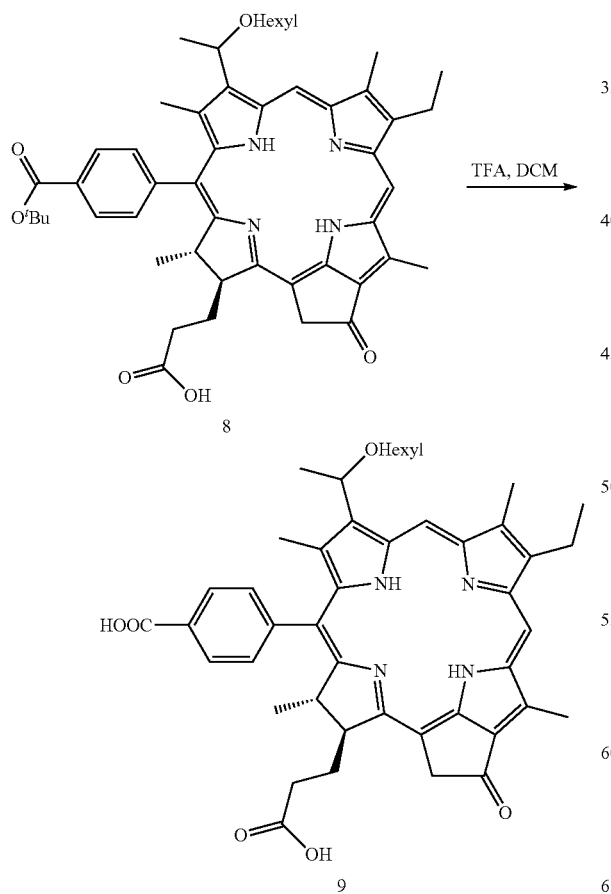

Compound 8 was dissolved in ~20 mL CH$_2$Cl$_2$, and then put ~12 mL TFA. Under argon stirred for 2 hours. After work-up, the UV was 670 nm. Purify the compound by 10% MeOH/CH$_2$Cl$_2$. The desired compound was obtained in 40% yield (51.5 mg). UV-visible, $\lambda_{max}$ (CHCl$_3$), nm (ε): 670 nm (4.45×10$^4$), 551 nm (1.61×10$^4$), 416 nm (10.5×10$^4$). $^1$HNMR (CDCl$_3$ and CD$_3$OD; 400 MHz): δ 7.91 (s, 1H, 5-H), 7.63 (m, 1H, 10-H), 7.08 (m, 1H, Ar—H), 6.84 (s, 2H, Ar—H), 6.74 (m, 1H, Ar—H), 5.80 (m, 1H, 3$^1$-H), 5.43-5.00 (m, 4H, 2H for 13$^2$-CH$_2$, 2H for 17-H and 18-H), 3.87-3.57 (m, 7H, 2H for 3$^1$-OCH$_2$(CH$_2$)$_4$CH$_3$, 2H for 8-CH$_2$CH$_3$, 3H for 7-CH$_3$), 3.53 (m, 3H, 2-CH$_3$), 3.38 (s, 3H, 12-CH$_3$), 2.69-2.41 (m, 2H, 17$^1$-H), 2.40-2.30 (d, J=3.1 Hz, 3H, 3$^2$-CH$_3$), 2.27-2.17 (m, 2H, 17$^2$-H), 2.15 (d, J=7.0 Hz, 3H, 18-H), 2.08-1.92 (m, 5H, 3H for 8-CH$_2$CH$_3$, 2H for 3$^1$-OCH$_2$CH$_2$(CH$_2$)$_3$CH$_3$), 1.47-1.18 (m, 6H, 3$^1$-O(CH$_2$)$_2$(CH$_2$)$_3$CH$_3$), 0.89 (m, 3H, 3$^1$-OCH$_2$(CH$_2$)$_4$CH$_3$). Mass calcd for C$_{46}$H$_{52}$N$_4$O$_6$: 756.4. found: 756.7.

Synthesis of 10

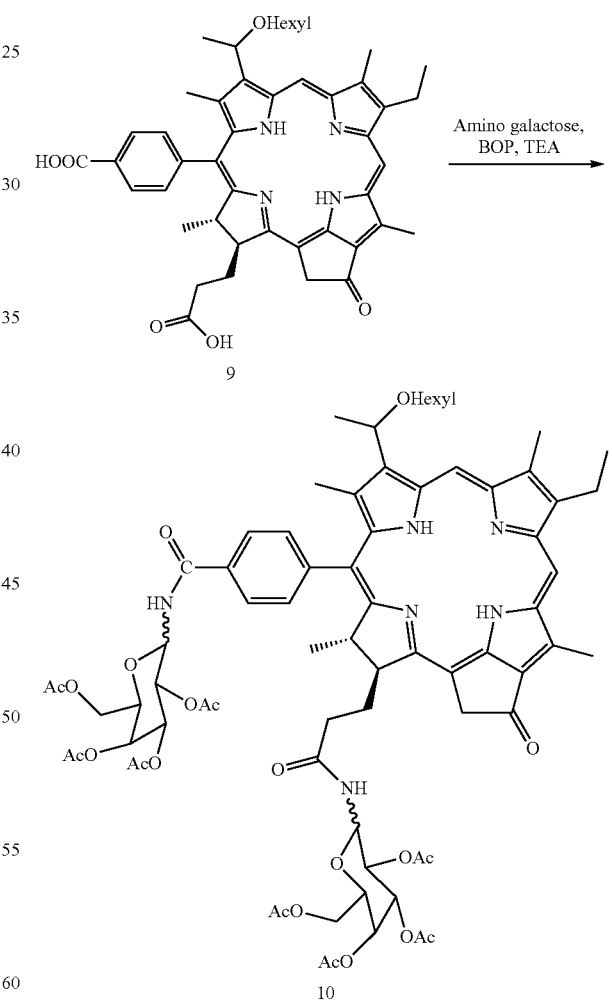

Compound 9 (40 mg, 0.056 mmole, 1.0 eq) was dissolved in DMF (6 ml). To it was added BOP (93 mg, 0.210 mmole, 4.0 eq) and amino galactose (73 mg, 0.210 mmole, 4.0 eq) and few drops of triethyl amine. Stirred for overnight at room temperature. The DMF was then removed under vacuum. The resulting film was then reconstituted in 50 mL of dichloromethane. The solution was then washed with sat. NaHCO$_3$/water/brine (100 mL×1 each) and dried over sodium sulfate and the solvent was removed under pressure. The resulting crude product was purified using preparative plate using methanol and DCM to give product 10. Yield=30 mg; UV-vis λ max (in CH$_2$Cl$_2$): 671, 617, 547, 516, 415; $^1$H NMR (CDCl$_3$): δ 10.13 & 10.17 (s, 1H, meso-H), 9.52 (s, 1H, meso-H); 8.19-8.28, 8.02-8.05, 7.63-7.74 (Phenyl ring protons, 4H), 6.03-6.07 (m, 1H, CONH), 5.79-5.84 (q, 1H CH(O-hexyl)-CH$_3$), 5.56-5.61 (m, 2H, galactose), 5.31-5.38 (m, 3H, galactose), 5.20 (s, 2H, 13$^1$CH$_2$), 5.15-5.18 (m, 1H, galactose), 5.05-5.09 (m, 1H, galactose), 4.87-4.93 (m, 1H, galactose), 4.20-4.26 (m, 4H, galactose OCH$_2$), 4.15-4.17 (m, 1H, 17H), 3.96-4.03 (m, 3H, 18H+2H galactose), 3.75-3.66 (m, 3H, 8CH$_2$+1H of 3$^1$ OCH$_2$), 3.65, 3.29, 2.31 (s, 3H each, 2-CH$_3$, 7-CH$_3$ and 12-CH$_3$), 2.23, 2.20, 2.11, 2.07, 2.01, 1.96, 1.94 & 1.93 (each s, 3H, 8× galactose CH$_3$CO$_2$), 2.10-2.15 (m, 4H, 17$^1$ CH$_2$+17$^2$ CH$_2$), 1.78 (broad m, 3H, 18 CH$_3$), 1.73 (t, 3H, 8$^2$ CH$_3$), 1.0-1.2 (multiplets, 8H, 3$^2$-OCH$_2$CH$_2$CH$_2$ CH$_2$CH$_2$CH$_3$), 0.70 & 0.80 (m, 3H, 3$^2$-OCH$_2$CH$_2$CH$_2$ CH$_2$CH$_2$CH$_3$), −1.53 and −1.60 (each brs, 2H NH).

Synthesis of 11

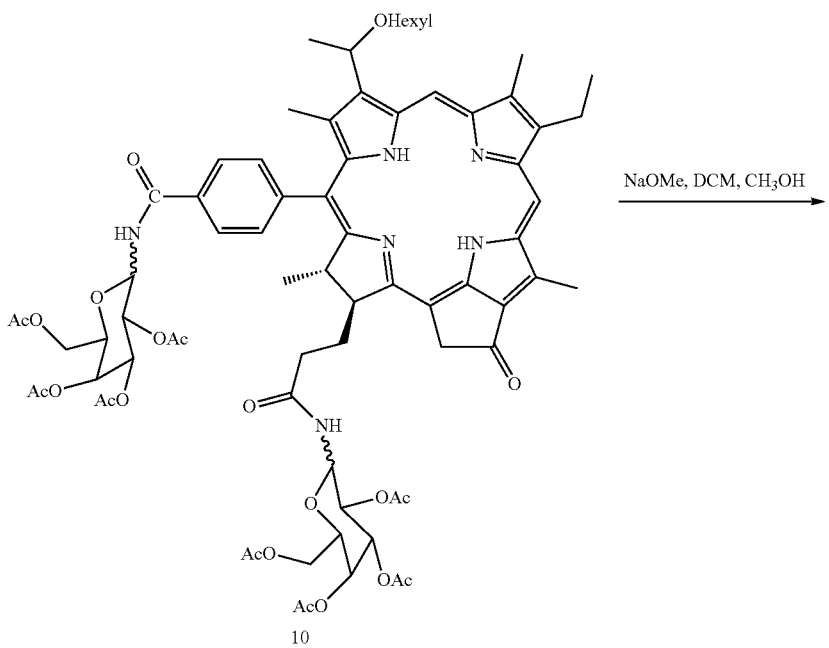

10

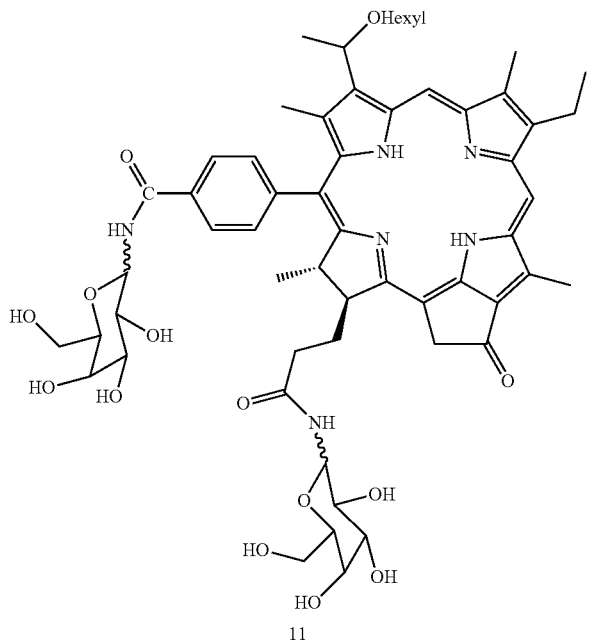

11

Compound 10 (15 mg, 0.02 mmol) was dissolved in DCM and methanol (1:10). To it was added 0.25 ml of sodium methoxide (0.5 M). Stirred for 1 hour under argon at room temperature. After the completion of reaction, the reaction mixture was neutralized with Dowex resin. After filtration, rotavaced the solvent and purified by preparative plate using 30% MeOH/DCM to get compound II in 40% yield. UV-vis λ max (in $CH_2Cl_2$): 671, 617, 547, 516, 415; $^1$H NMR ($CDCl_3$): δ 10.66 & 10.08 (s, 1H, meso-H), 9.52 (s, 1H, meso-H); 8.9-9.0, 8.8-8.87, 8.34-8.38 (Phenyl ring protons, 4H), 6.32-6.37 (m, 1H, CONH), 5.95-5.98 (q, 1H CH(O-hexyl)-$CH_3$), 4.54-4.72, 4.41-4.48, 4.23-4.36 (multiplets 23H, 14H galactose+17H+18H, 4H of galactose $OCH_2$, 3H, $8CH_2+1H$ of $3^1$ $OCH_2$), 4.08-4.11 (1H of $8CH_2$), 4.23, 3.99, 3.87/3.85, 2.31 (s, 3H each, 2-$CH_3$, 7-$CH_3$ and 12-$CH_3$), 2.84-2.94 (m, 4H, $17^1$ $CH_2+17^2$ $CH_2$), 2.66-2.70 (d, 3H, $3CH_3$), 2.30-2.34 (broad m, 3H, 18 $CH_3$), 2.14-2.25 (m, 2H, $OCH_2CH_2CH_2$ $CH_2CH_2CH_3$), 1.70-1.73 (m, 3H, $8^2$ $CH_3$), 1.81-1.82, 1.35-1.38, 1.25-1.28 (multiplets, 9H, 6H of $3^2$-$OCH_2CH_2$ $CH_2CH_2CH_3$+3H of $3^2$-$OCH_2CH_2CH_2$ $CH_2CH_2CH_3$).

Synthesis of 12

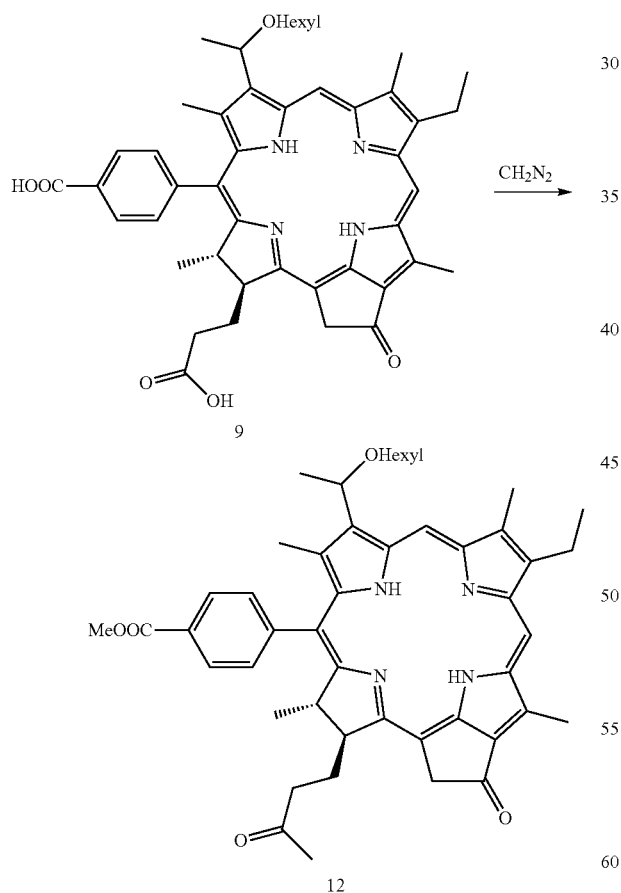

After treatment with diazomethane, compound 9 was converted into 12 quantitatively. NMR of compound 3: $^1$HNMR ($CDCl_3$; 400 MHz): δ 10.16, 10.12 (each for one singlet, altogether 1H, 5-H), 9.55 (s, 1H, 10-H), 8.45 (d, J=7.6 Hz, 1H, Ar—H), 8.30 (m, 1H, Ar—H), 8.23 (m, 1H, Ar—H), 7.73 (m, 1H, Ar—H), 5.81 (m, 1H, $3^1$-H), 5.35 (m, 2H, $13^2$-$CH_2$), 5.21 (m, 2H, 17-H and 18-H), 4.09 (s, 6H, 2×-$CH_3$), 3.79-3.61 (m, 7H, 2H for $3^1$-$OCH_2(CH_2)_4CH_3$, 2H for 8-$CH_2CH_3$, 3H for 7-$CH_3$), 3.57 (s, 3H, 2-$CH_3$), 3.29 (s, 3H, 12-$CH_3$), 2.58-2.38 (m, 2H, $17^1$-H), 2.34 (d, J=3.1 Hz, 3H, $3^2$-$CH_3$), 2.28-2.15 (m, 2H, $17^2$-H), 2.12 (d, J=7.0 Hz, 3H, 18-H), 2.08-1.94 (m, 5H, 3H for 8-$CH_2CH_3$, 2H for $3^1$-$OCH_2CH_2(CH_2)_3CH_3$), 1.39-1.20 (m, 6H, $3^1$-$O(CH_2)_2(CH_2)_3CH_3$), 1.02 (m, 3H, $3^1$-$OCH_2(CH_2)_4$—$CH_3$), −1.53 (s, 1H, —NH), −1.62 (s, 1H, —NH).

Graphs showing effect upon colon 26 cancer cells for compound 812 of the invention relative to compound 815 are illustrated in FIGS. 3-12.

Figure 3:
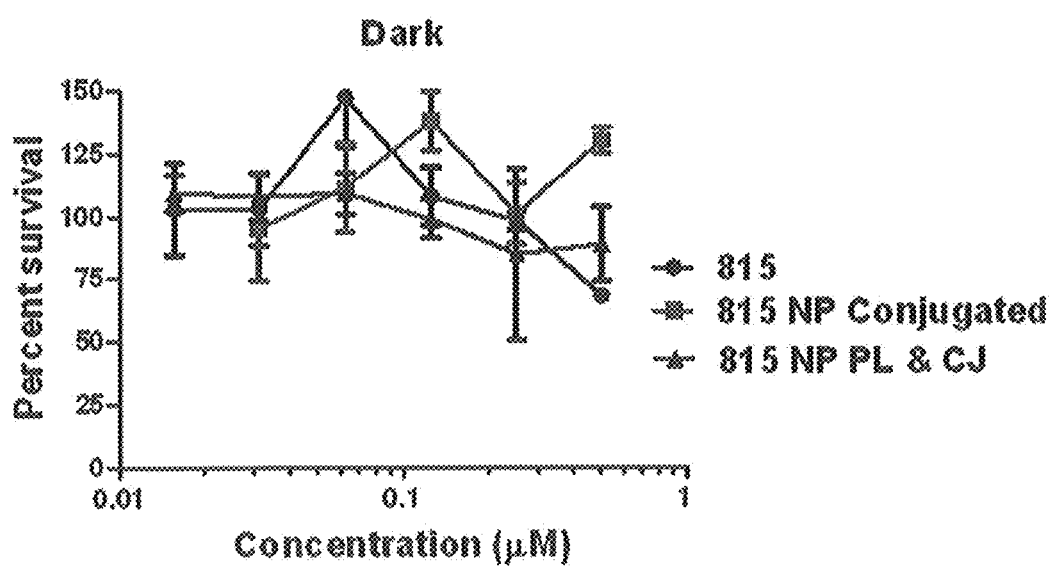
FIG. 3 is a graph showing percent survival of Colon 26 cancer cells relative to concentration in the form of MTT Assay of compound PS815 vs. PS815 conjugated to PAA nanoparticle vs. PS815 both conjugated and post-loaded on PAA nanoparticle without light treatment.
Figure 4:
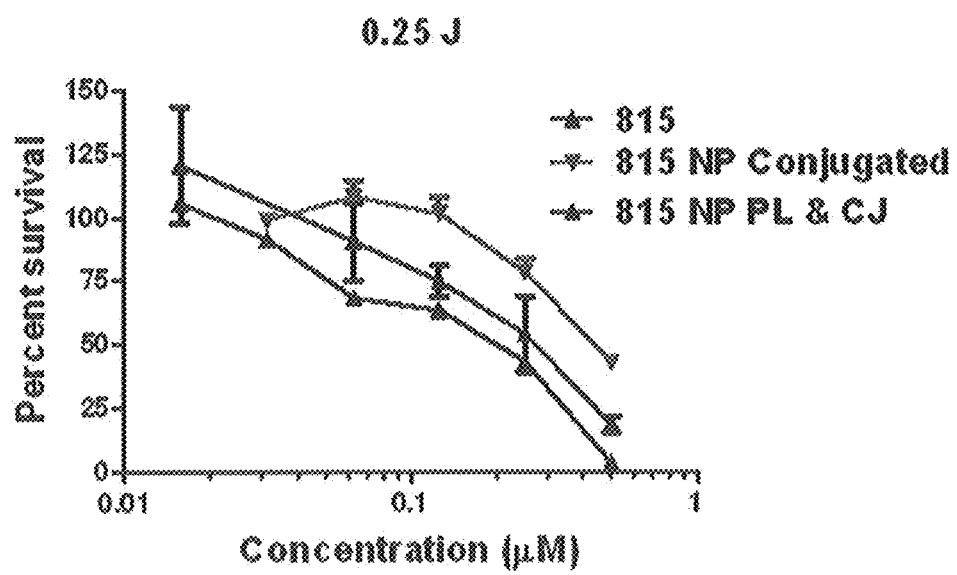
FIG. 4 is a graph showing percent survival of Colon 26 cancer cells relative to concentration in the form of MTT Assay of compound PS815 vs. PS815 conjugated to PAA nanoparticle vs. PS815 both conjugated and post-loaded on PAA nanoparticles. Light treatment was done at 0.25 Joules following 24 h incubation in Colon 26 cells.
Figure 5:
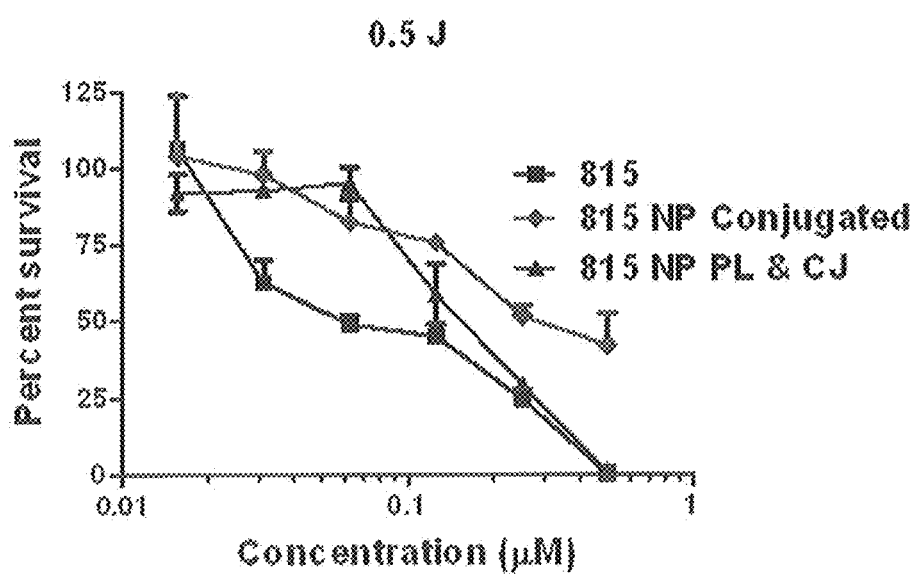
FIG. 5 is a graph showing percent survival of Colon 26 cancer cells relative to concentration in the form of MTT Assay of compound PS815 vs. PS815 conjugated to PAA nanoparticle vs. PS815 both conjugated and post-loaded on PAA nanoparticles. Light treatment was done at 0.5 Joules following 24 h incubation in Colon 26 cells.
Figure 6:
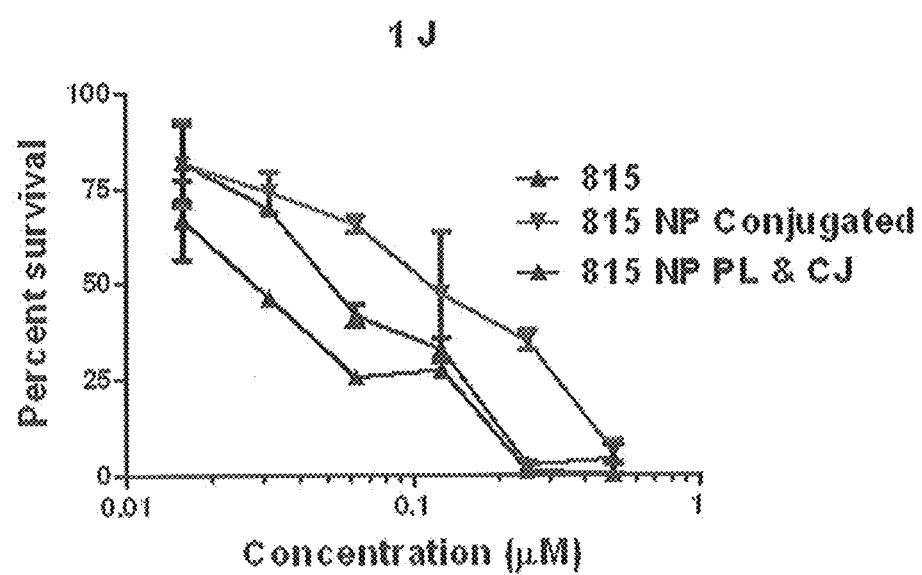
FIG. 6 is a graph showing percent survival of Colon 26 cancer cells relative to concentration in the form of MTT Assay of compound PS815 vs. PS815 conjugated to PAA nanoparticle vs. PS815 both conjugated and post-loaded on PAA nanoparticles. Light treatment was done at one Joule following 24 h incubation in Colon 26 cells.
Figure 7:
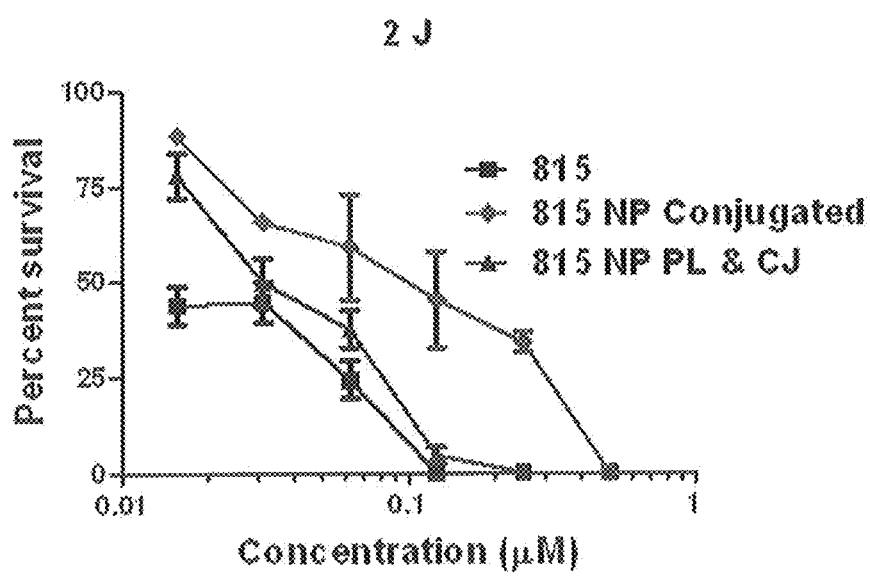
FIG. 7 is a graph showing percent survival of Colon 26 cancer cells relative to concentration in the form of MTT Assay of compound PS815 vs. PS815 conjugated to PAA nanoparticle vs. PS815 both conjugated and post-loaded on PAA nanoparticles. Light treatment was done at 2 Joules following 24 h incubation in Colon 26 cells.
Figure 8:
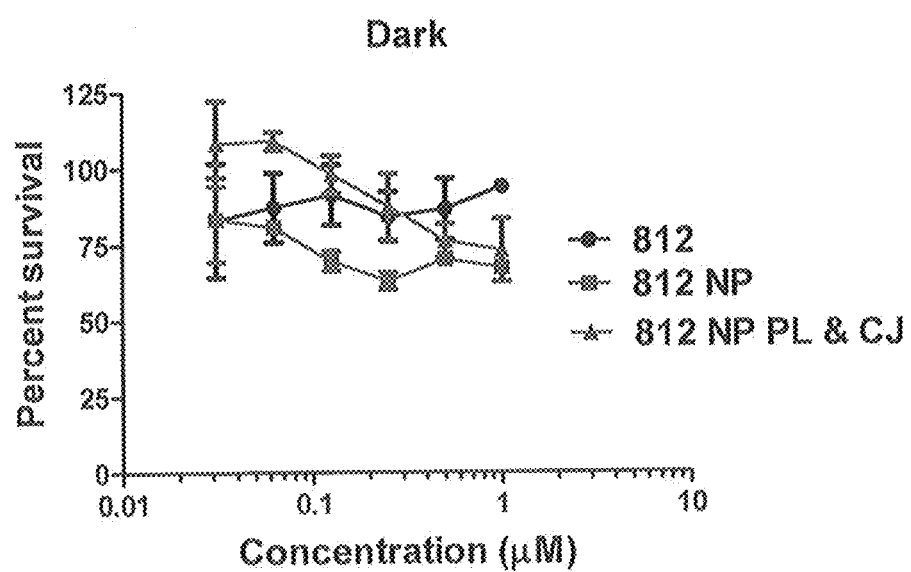
FIG. 8 is a graph showing percent survival of Colon 26 cancer cells relative to concentration in the form of MTT Assay of compound PS812 of the invention vs. PS812 conjugated to PAA nanoparticle vs. PS812 both conjugated and post-loaded on PAA nanoparticles without light treatment.
Figure 9:
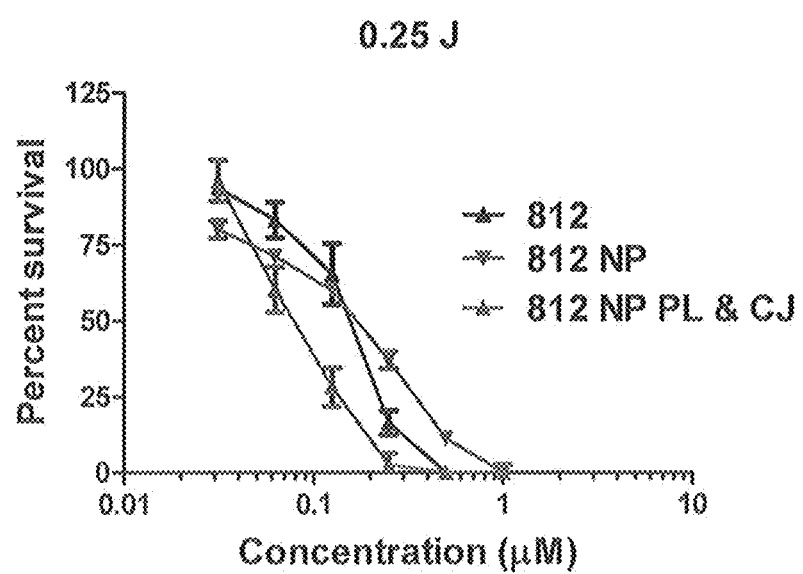
FIG. 9 is a graph showing percent survival of Colon 26 cancer cells relative to concentration in the form of MTT Assay of compound PS812 of the invention vs. PS812 conjugated to PAA nanoparticle vs. PS812 both conjugated and post-loaded on PAA nanoparticles. Light treatment was done at 0.5 Joules following 24 h incubation in Colon 26 cells.
Figure 10:
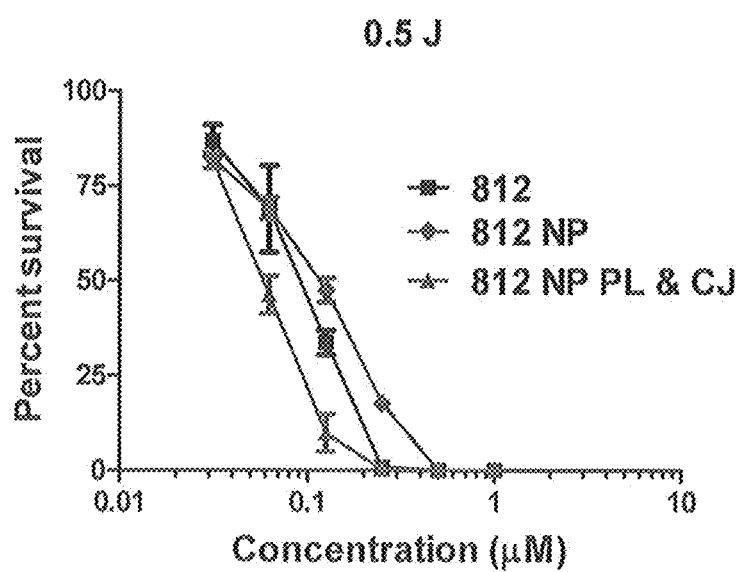
FIG. 10 is a graph showing percent survival of Colon 26 cancer cells relative to concentration in the form of MTT Assay of compound PS812 of the invention vs. PS812 conjugated to PAA nanoparticle vs. PS812 both conjugated and post-loaded on PAA nanoparticles. Light treatment was done at 0.5 Joule following 24 h incubation in Colon 26 cells.
Figure 11:
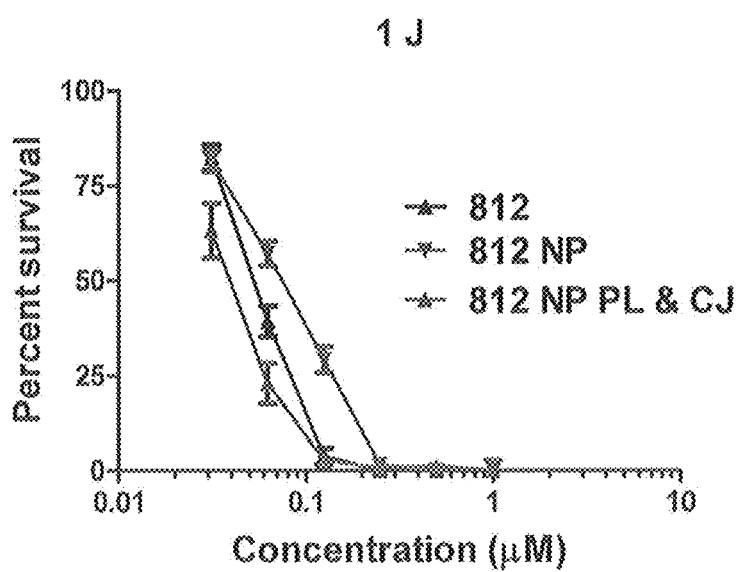
FIG. 11 is a graph showing percent survival of Colon 26 cancer cells relative to concentration in the form of MTT Assay of compound PS812 of the invention vs. PS812 conjugated to PAA nanoparticle vs. PS812 both conjugated and post-loaded on PAA nanoparticles. Light treatment was done at one Joule following 24 h incubation in Colon 26 cells.
Figure 12:
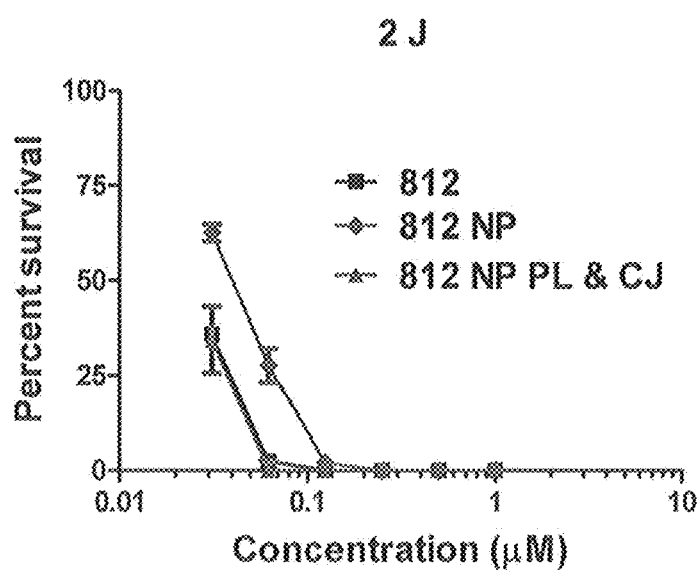
FIG. 12 is a graph showing percent survival of Colon 26 cancer cells relative to concentration in the form of MTT Assay of compound PS812 of the invention vs. PS812 conjugated to PAA nanoparticle vs. PS812 both conjugated and post-loaded on FAA nanoparticles. Light treatment was done at 2 Joules following 24 h incubation in Colon 26 cells.

In particular, FIG. 3 shows an MTT assay of compound 815 vs. 815 conjugated to PAA nanoparticles and post loaded, non conjugated on PAA nanoparticles. Light treatment was done following 24 hour incubation in colon 26 cells. The MTT assay is a colorimetric assay for measuring the activity of cellular enzymes that reduce MTT to dye resulting in a purple color. The MIT assay is used to determine toxicity of substances to cells.

As can be seen from FIG. 3-7, conjugation of PS815 with nanoparticles reduces its toxicity to the tumor cells.

By contrast, as shown in FIGS. 8-12, conjugation of PS812 of the invention unexpectedly increases toxicity to the cancer cells.

FIGS. 9-12 illustrate the unexpectedly superior fluorescent imaging of compound PS812 of the invention relative to compound PS815.

Figure 13:
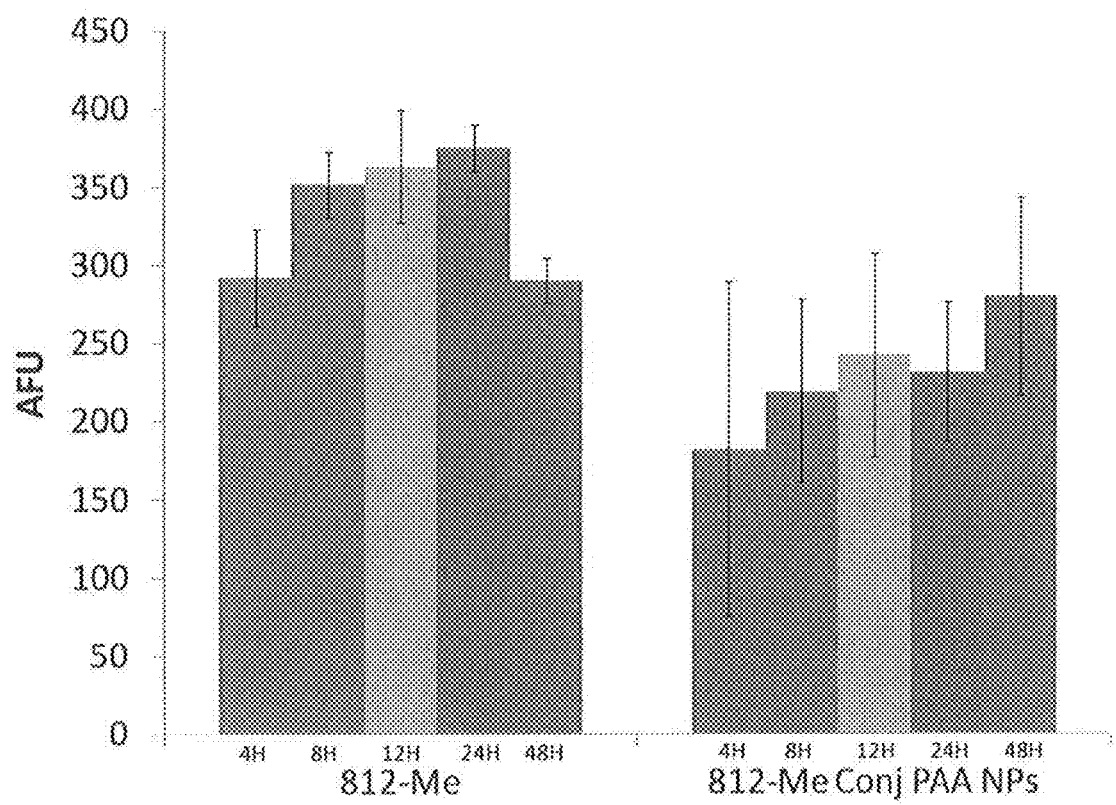
FIG. 13 is a bar graph showing that the superior treatment and imaging activity of PS812 conjugated to PAA nanoparticles surprisingly occurs despite lower accumulation of the material in the cells.
Figure 14:
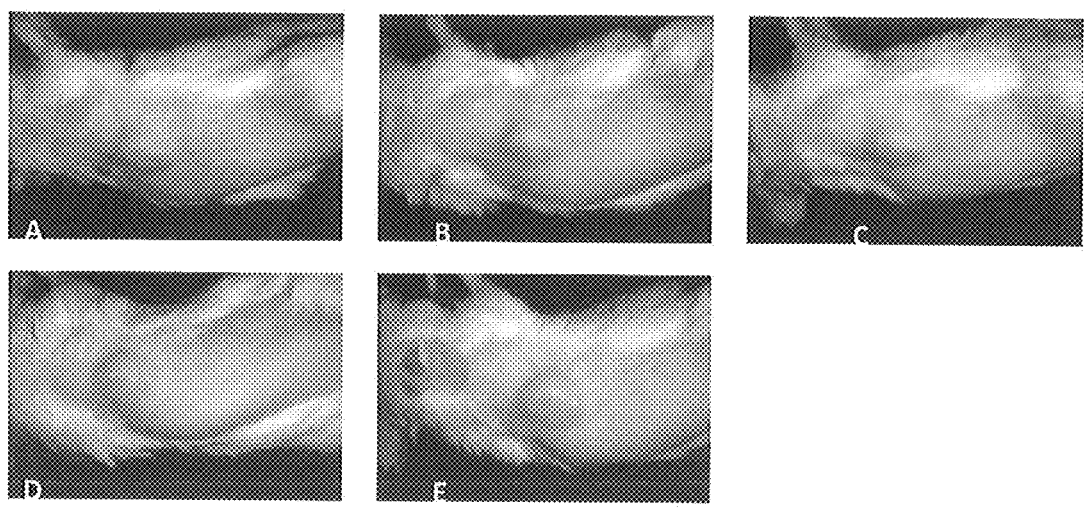
FIG. 14 shows a series of A through E fluorescent images, using a Maestro GNIR-Flex™ in vivo imaging system, at 4, 8, 12, 24 and 48 hours post i.v. 0.47 mmoles/kg injection of Balb/c mice having an induced COLO-26 tumor, The excitation wave length was 575-605 nm and emission wave length was 645 nm long pass. The images are color enhanced by computer assignment of color depth relative to fluorescent intensity. Exposure was 100 ms (fluorescence 0 and 8 ms 9 white light). The injected material used was PS 812-ME, neither conjugated nor post loaded on nanoparticles.
Figure 15:
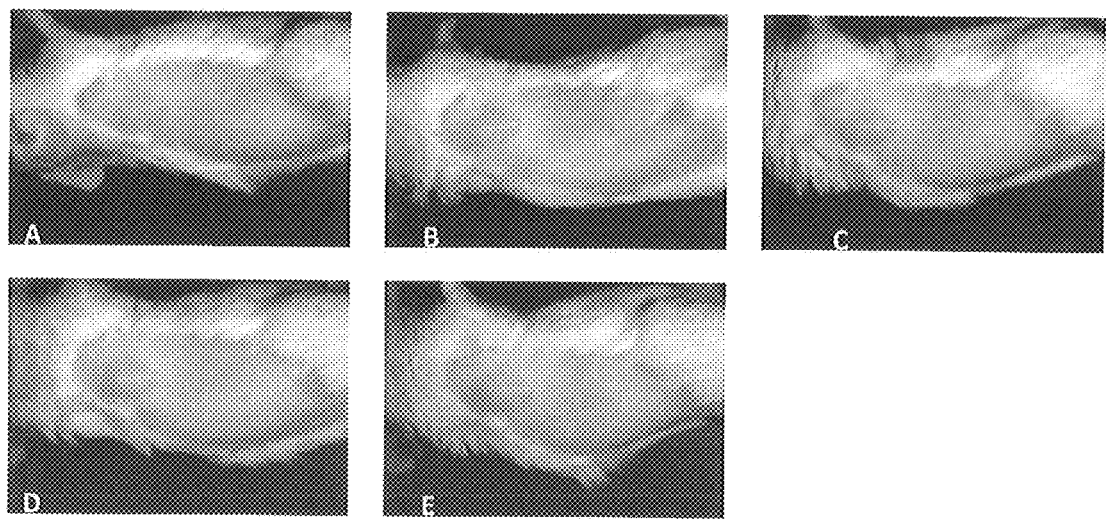
FIG. 15 shows a series of A through E fluorescent images, using a Maestro GNIR-Flex™ in vivo imaging system, at 4, 8, 12, 24 and 48 hours post i.v. 0.47 mmoles/kg injection of Balb/c mice having an induced COLO-26 tumor, The excitation wave length was 575-605 nm and emission wave length was 645 nm long pass. The images are color enhanced by computer assignment of color depth relative to fluorescent intensity. Exposure was 100 ms (fluorescence and 8 ms (white light) The injected material used was PS 812-Me (compound 12) conjugated to FAA nanoparticles as shown in FIG. 2. Image clarity and definition relative to unconjugated PS812Me is apparent.
Figure 16:
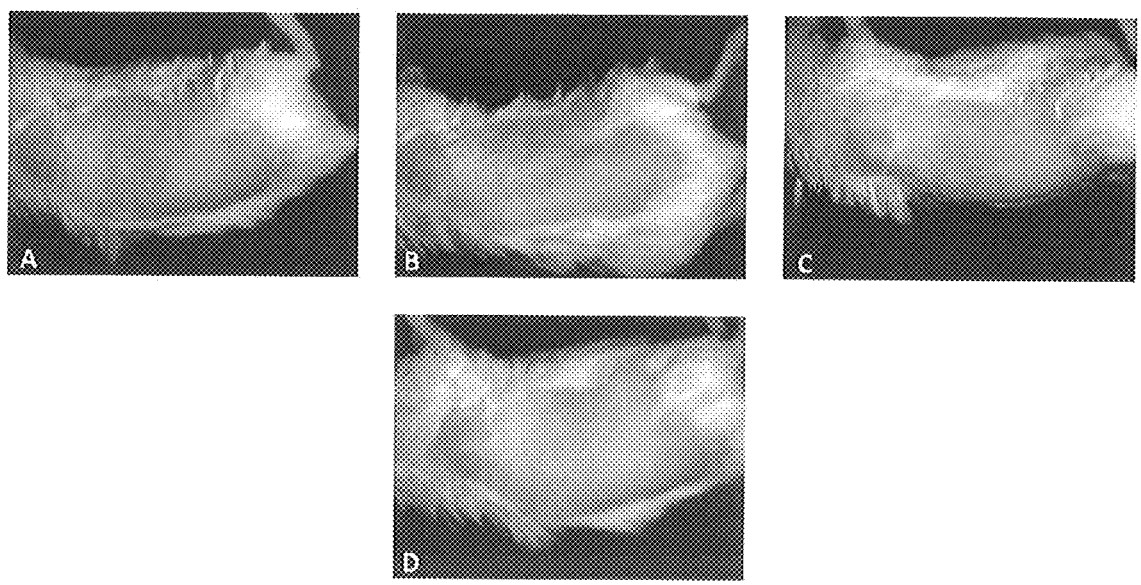
FIG. 16 shows a series of A through D fluorescent images, using a Maestro GNIR-Flex™ in vivo imaging system, at 4, 10, 24 and 48 hours post i.v. 0.47 mmoles/kg injection of Balb/c mice having an induced COLO-26 tumor, The excitation wave length was 575-605 nm and emission wave length was 645 nm long pass. The images are color enhanced by computer assignment of color depth relative to fluorescent intensity. Exposure was 100 ms (fluorescence and 8 ms (white light) The injected material used was PS 812-Me (compound 12) conjugated to PAA nanoparticles as shown in FIG. 2 and cyanine dye (CD) conjugated to PAA nanoparticles. Image clarity and definition relative to unconjugated PS812Me and to PS 812-Me (compound 12) conjugated to PAA nanoparticles, is apparent.
Figure 17:
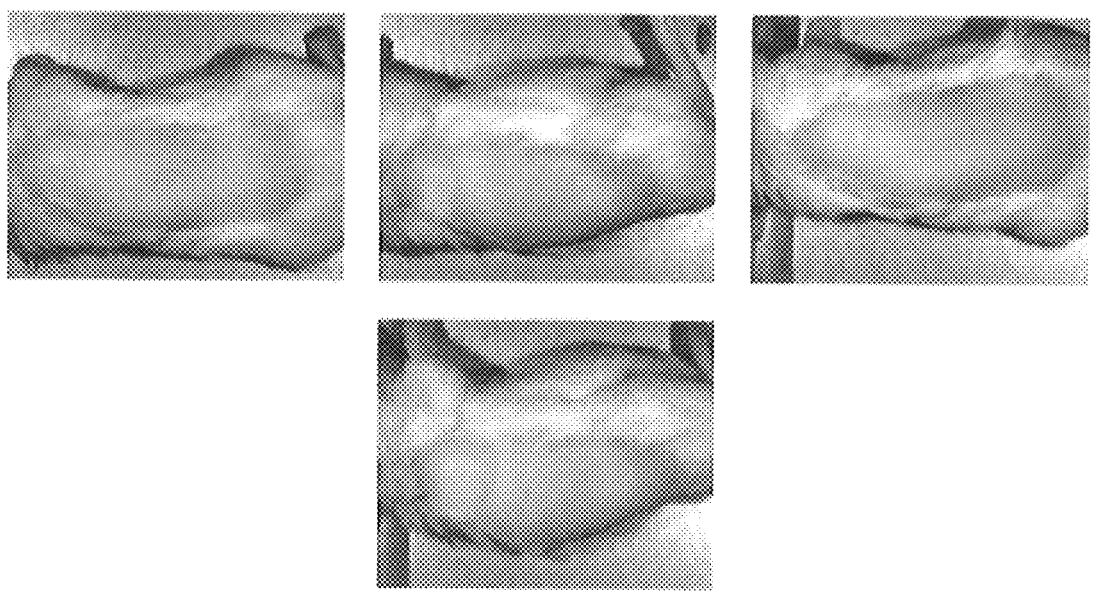
FIG. 17 shows a series of A through D fluorescent images, using a Maestro GNIR-Flex™ in vivo imaging system, at 4, 10, 24 and 48 hours post i.v. 0.47 mmoles/kg injection of Balb/c mice having an induced COLO-26 tumor, The excitation wave length was 575-605 nm and emission wave length was 645 nm long pass. The images are color enhanced by computer assignment of color depth relative to fluorescent intensity. Exposure was 100 ms (fluorescence and 8 ms (white light) The injected material used was PS 815 (FIG. 1) conjugated to PAA nanoparticles as shown in FIG. 1 and cyanine dye (CD) conjugated to PAA nanoparticles. The inferior image is apparent relative to image clarity and definition relative to PS812-Me (compound 12) conjugated to FAA nanoparticles and relative to PS812 conjugated to PAA nanoparticles as shown in FIG. 1 and cyanine dye (CD) conjugated to PAA nanoparticles.

FIG. 13 shows that the superior treatment and imaging activity of PS812 conjugated to PAA nanoparticles surprisingly occurs despite lower accumulation of the material in the cells.

FIGS. 14-17 show superiority of fluorescence imaging using PS812 compound of the invention.

We claim:
1. A tetrapyrrolic photosensitizer having the structural formula:

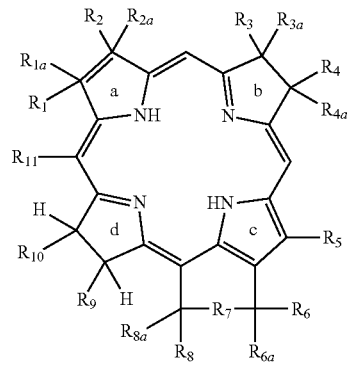

or a pharmaceutically acceptable derivative thereof, wherein:
$R_1$ is hydrogen or lower alkyl of 1 through 8 carbon atoms;
$R_2$ is hydrogen, lower alkyl of 1 through 8 carbon atoms, —C(O)$R_a$ or —COOR$_a$ or —CH($CH_3$)(OR$_a$) or —CH($CH_3$)(O($CH_2$)$_n$XR$_a$) where R$_a$ is hydrogen, lower alkyl of 1 through 8 carbon atoms, alkenyl of 1 through 8 carbon atoms, cycloalkyl; —CH=CH$_2$, —CH(OR$_{20}$)CH$_3$, —C(O)Me, —C(=NR$_{20}$)CH$_3$ or —CH(NHR$_{20}$)CH$_3$ where X is an aryl or heteroaryl group;

n is an integer of 0 to 6;

where R$_{20}$ is lower alkyl of 1 through 8 carbon atoms, or 3,5-bis(trifluoromethyl)-benzyl; and R$_{1a}$ and R$_{2a}$ are each independently hydrogen or lower alkyl of 1 through 8 carbon atoms, or together form a covalent bond;

R$_3$ and R$_4$ are each independently hydrogen or lower alkyl of 1 through 8 carbon atoms;

R$_{3a}$ and R$_{4a}$ are each independently hydrogen or lower alkyl of 1 through 8 carbon atoms, or together form a covalent bond;

R$_5$ is hydrogen;

R$_6$ and R$_{6a}$ are each independently hydrogen or lower alkyl of 1 through 8 carbon atoms, or together form =O;

R$_7$ is a covalent bond, alkylene of 1 through 3 carbon atoms, azaalkyl, or azaaraalkyl or =NR$_{21}$ where R$_{21}$ is 3,5-bis(tri-fluoromethyl)benzyl or —CH$_2$Y—R' or —YR' where Y is an aryl or heteroaryl group;

R$_8$ and R$_{8a}$ are each independently hydrogen or lower alkyl of 1 through 8 carbon atoms or together form =O;

R$_9$ and R$_{10}$ are each independently hydrogen, or lower alkyl of 1 through 8 carbon atoms and R$_9$ may be —CH$_2$CH$_2$COOR$^2$ where R$^2$ is hydrogen or an alkyl group that may optionally substituted with one or more fluorine atoms;

R$_{11}$ is Br or phenyl where each of R$_1$-R$_{10}$ and R$_{11}$, when R$_{11}$ is phenyl, may be substituted with one or more substituents each independently selected from a PAA or amine functionalized PAA nanoparticle or Q, where Q is alkyl, haloalkyl, halo, or —COOR$_b$ where R$_b$ is hydrogen, alkyl, alkenyl, alkynyl, cycloalkyl, aryl, heteroaryl, araalkyl, or OR$_c$ where R$_c$ is hydrogen, alkyl, alkenyl, alkynyl, cycloalkyl, or aryl or CONR$_d$R$_e$ where R$_d$ and R$_e$ are each independently hydrogen, alkyl, alkenyl, alkynyl, cycloalkyl, or aryl, or NR$_f$R$_g$ where R$_f$ and R$_g$ are each independently hydrogen, alkyl, alkenyl, alkynyl, cycloalkyl, or aryl, or =NR$_h$ where R$_h$ is hydrogen, alkyl, alkenyl, alkynyl, cycloalkyl, or aryl, or is an amino acid residue;

each Q is independently unsubstituted or is substituted with one or more substituents each independently selected from Q$_1$, where Q$_1$ is alkyl, haloalkyl, halo, or —COOR$_b$ where R$_b$ is hydrogen, alkyl, alkenyl, alkynyl, cycloalkyl, aryl, heteroaryl, araalkyl, or OR$_c$ where R$_c$ is hydrogen, alkyl, alkenyl, alkynyl, cycloalkyl, or aryl or CONR$_d$R$_e$ where R$_d$ and R$_e$ are each independently hydrogen, alkyl, alkenyl, alkynyl, cycloalkyl, or aryl, or NR$_f$R$_g$ where R$_f$ and R$_g$ are each independently hydrogen, alkyl, alkenyl, alkynyl, cycloalkyl, or aryl, or =NR$_h$ where R$_h$ is hydrogen, alkyl, alkenyl, alkynyl, cycloalkyl, or aryl, or is an amino acid residue.

and further provided that, when a substituent contains a carboxy group, the carboxy group may be substituted with an amine group to form an amide.

2. The compound of claim 1 having the formula:

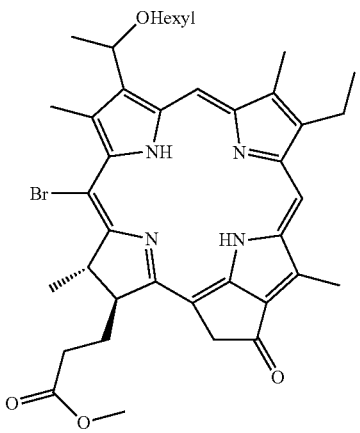

3. The compound of claim 1 having the formula:

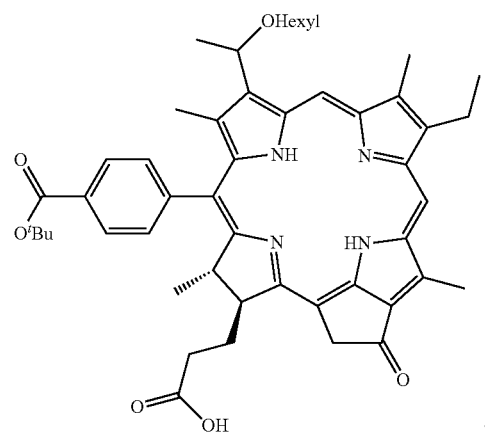

4. The compound of claim 1 having the formula:

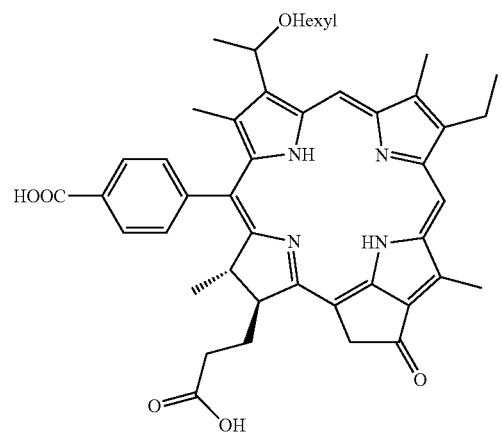

5. The compound of claim 1 having the formula:
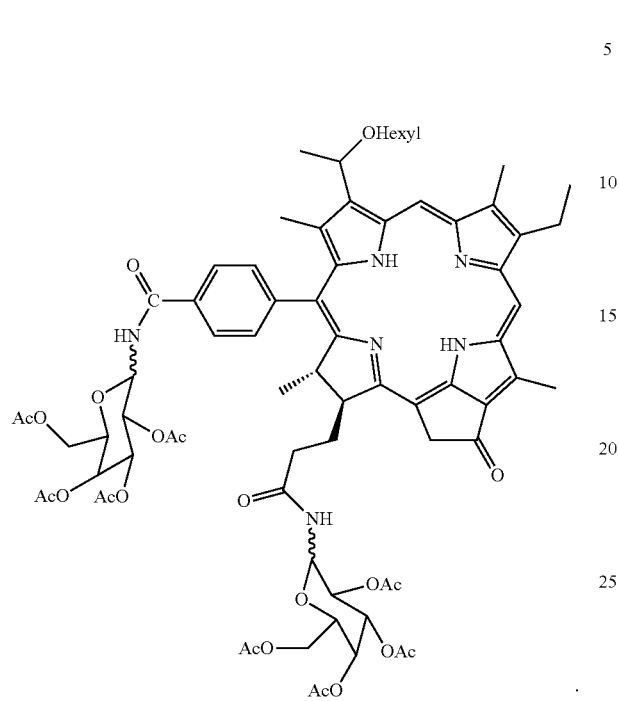
6. The compound of claim 1 having the formula:
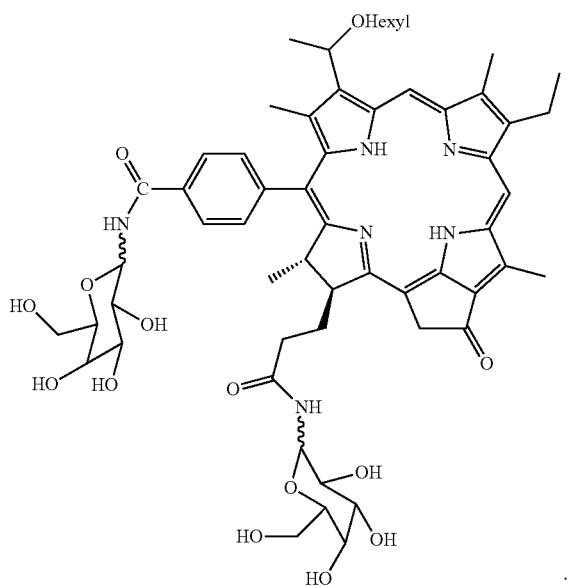
7. The compound of claim 1 having the formula:
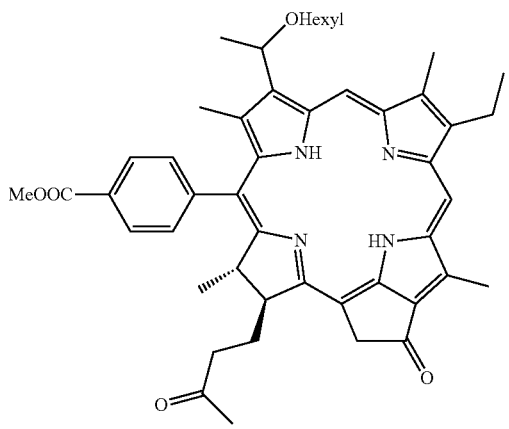
8. The compound of claim 1 having the formula:
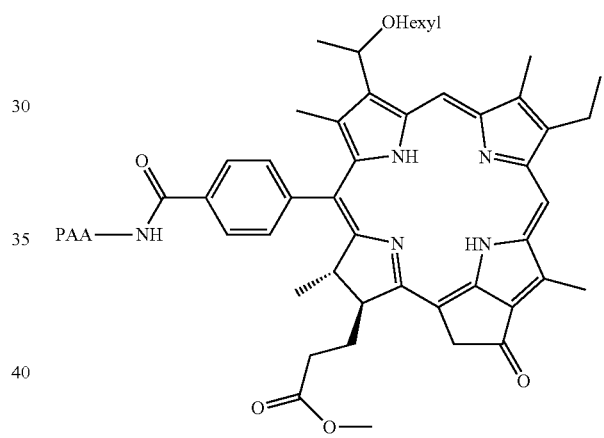
9. The compound of claim 1 having the formula:
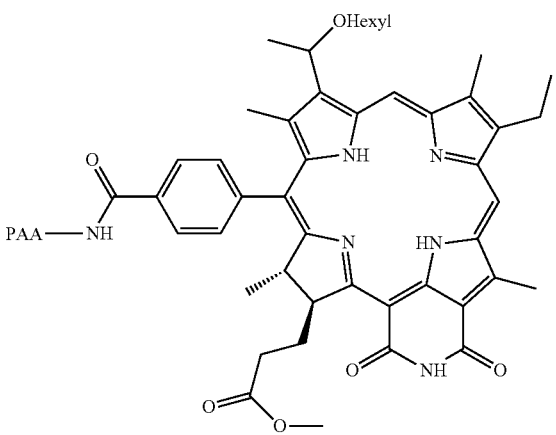

10. The compound of claim 1 having the formula:
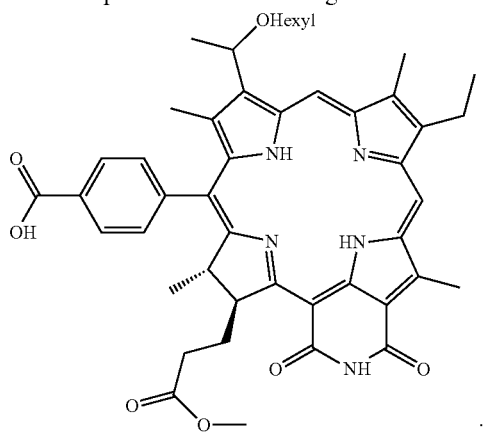
11. The compound of claim 1 having the formula:
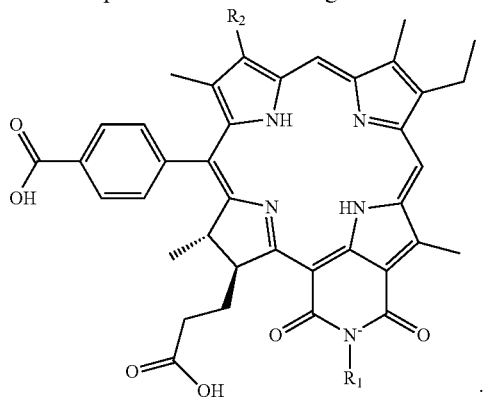
12. A conjugate of the compound of claim 1 with a PAA nanoparticle, having the formula:
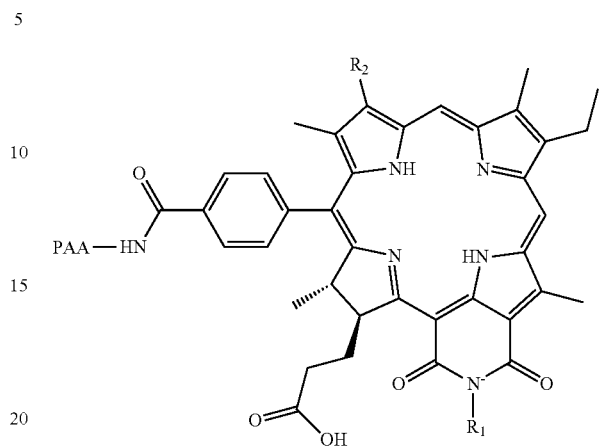
13. A conjugate of the compound of claim 1 with a PAA nanoparticle.
14. The compound of claim 1 where $R_{11}$ is -phenyl-$CONH_2$ conjugated with a PAA nanoparticle to form —CONH-PAA.
* * * * *